United States Patent [19]

Pfister et al.

[11] 3,963,753

[45] June 15, 1976

[54] DISUBSTITUTED XANTHONE CARBOXYLIC ACID COMPOUNDS

[75] Inventors: Jurg R. Pfister, Los Altos; Ian T. Harrison; John H. Fried, both of Palo Alto, all of Calif.

[73] Assignee: Syntex (U.S.A.) Inc., Palo Alto, Calif.

[22] Filed: Mar. 13, 1975

[21] Appl. No.: 558,023

Related U.S. Application Data

[60] Division of Ser. No. 431,794, Jan. 8, 1974, Pat. No. 3,894,049, which is a continuation-in-part of Ser. No. 259,852, June 5, 1972, abandoned, which is a continuation-in-part of Ser. No. 217,287, Jan. 12, 1972, Pat. No. 3,849,565.

[52] U.S. Cl............................ 260/335; 260/211 R; 260/268 R; 260/293.58
[51] Int. Cl.$^2$........................................ C07D 311/86
[58] Field of Search.................................. 260/335

[56] References Cited

UNITED STATES PATENTS

| | | | |
|---|---|---|---|
| 3,642,997 | 2/1972 | Shen et al. | 424/250 |
| 3,706,768 | 12/1972 | Bays | 260/335 |

*Primary Examiner*—Norma S. Milestone
*Attorney, Agent, or Firm*—Gerard A. Blaufarb; William B. Walker

[57] ABSTRACT

Compositions containing and methods employing, as the essential ingredient, novel disubstituted xanthone carboxylic acid compounds which are useful in the treatment of allergic conditions. Methods for preparing these compounds and compositions and intermediates therein are also disclosed. 5-Methyl-sulfinyl-7-isopropoxyxanthone-2-carboxylic acid and 5,7-di(methylsulfinyl)xanthone-2-carboxylic acid are illustrated as representative compounds.

7 Claims, No Drawings

DISUBSTITUTED XANTHONE CARBOXYLIC ACID COMPOUNDS

This is a division of application Ser. No. 431,794, filed Jan. 8, 1974 and now U.S. Pat. No. 3,894,049, which is in turn a continuation-in-part of application Ser. No. 259,852, filed June 5, 1972, now abandoned, in turn a continuation-in-part of application Ser. No. 217,287, filed Jan. 12, 1972 and now U.S. Pat. No. 3,849,565.

The present invention is directed to novel disubstituted xanthone carboxylic acid compounds and to compositions containing and methods utilizing these compounds as the essential ingredient in the treatment of symptoms associated with allergic manifestations, for example, asthmatic conditions.

In a first aspect, the present invention relates to novel C-5,7 disubstituted xanthone-2-carboxylic acid compounds selected from those represented by the following formulas:

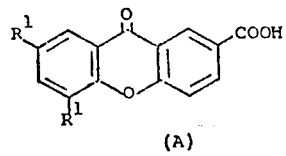
(A)

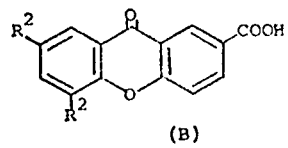
(B)

and the pharmaceutically acceptable, non-toxic esters, amides, and salts thereof;

wherein the $R^1$ groups are identical and selected from 1-hydroxylower alkyl and lower alkyl, cycloalkyl, tetrahydrofuran-2-yl, tetrahydropyran-2-yl, tetrahydropyran-4-yl, and 4-alkoxytetrahydropyran-4-yl, ethers thereof and the carboxylic acyl esters thereof; lower alkanoyl; and the group

in which $n$ is the integer 1 or 2, R is lower alkyl when $n$ is 1 and R is lower alkyl, hydroxy, amino, monolower alkylamino, or dilower alkylamino when $n$ is 2; and one $R^2$ group is selected from alkyl and alkoxy and the other $R^2$ group is selected from 1-hydroxylower alkyl and the lower alkyl, cycloalkyl, tetrahydrofuran-2-yl, tetrahydropyran-2-yl, tetrahydropyran-1-yl and 4-alkoxytetrahydropyran-4-yl ethers thereof and the carboxylic acyl esters thereof; lower alkanoyl; and the group

in which each of $n$ and R is as defined above.

Thus included within the scope of the present invention are:
1. the C-5,7 disubstituted xanthone-2-carboxylic acid compounds wherein the substituents are identical and as defined by $R^1$ above, and
2. the C-5,7 disubstituted xanthone-2-carboxylic acid compounds wherein the substituents are different and as defined by $R^2$ above.

Those of class 1) include the 5,7-di(1-hydroxylower alkyl)-xanthone-2-carboxylic acid compounds and the lower alkyl, cycloalkyl, tetrahydrofuran-2-yl, tetrahydropyran-2-yl, tetrahydropyran-4-yl and 4-alkoxytetrahydropyran-4ethers (preferably methoxy) and esters (preferably acetoxy) thereof;

5,7-di(lower alkanoyl)xanthone-2-carboxylic acid compounds, 5,7-di(lower alkyl sulfinyl)xanthone-2-carboxylic acid compounds, 5,7-di(lower alkyl sulfonyl)xanthone-2-carboxylic acid compounds, 5,7-di(sulfo)xanthone-2-carboxylic acid compounds, 5,7-di(sulfamoyl)xanthone-2-carboxylic acid compounds, 5,7-di(N-monolower alkyl sulfamoyl)xanthone-2-carboxylic acid compounds, and 5,7-di(N,N-dilower alkyl sulfamoyl)xanthone-2-carboxylic acid compounds, represented respectively by the following formulas A-1 to A-6:

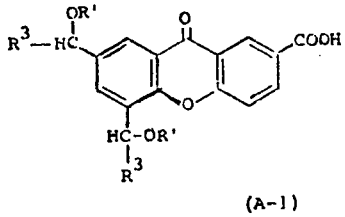
(A-1)

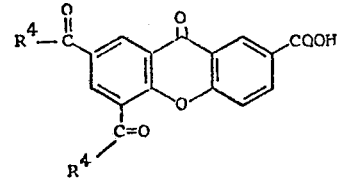
(A-2)

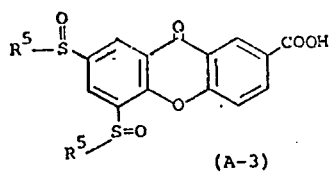
(A-3)

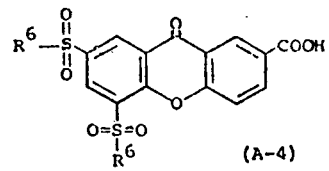
(A-4)

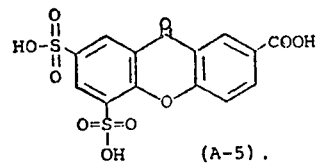
(A-5)

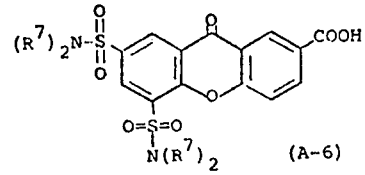
(A-6)

and the pharmaceutically acceptable, non-toxic esters, amides, and salts thereof; wherein R' is hydrogen, lower alkyl, cycloalkyl, tetrahydrofuran-2-yl, tetrahydropyran-2-yl, tetrahydropyran-4-yl, 4-alkoxytetrahydropyran-4-yl, or carboxylic acyl containing up to 12 carbon atoms; and each $R^3$, each $R^4$, each $R^5$, and each $R^6$ is lower alkyl and each $R^7$ is hydrogen or lower alkyl.

Those of class 2) include the 5-alkyl-7-($R^8$)-xanthone-2-carboxylic acid compounds, 5-alkoxy-7-($R^8$)-xanthone-2-carboxylic acid compounds, 7-alkyl-5-($R^8$)-xanthone-2-carboxylic acid compounds and 7-alkoxy-5-($R^8$)-xanthone-2-carboxylic acid compounds, wherein $R^8$ is 1-hydroxylower alkyl and the lower alkyl, cycloalkyl, tetrahydrofuran-2-yl, tetrahydropyran-2-yl, tetrahydropyran-4-yl and 4-alkoxytetrahydropyran-4-yl ethers thereof and the carboxylic acyl esters thereof (preferably methoxy ether and acetoxy ester); lower alkanoyl; lower alkylsulfinyl; lower alkylsulfonyl; sulfo; sulfamoyl; N-monolower alkylsulfamoyl; or N,N-dilower alkylsulfamoyl; represented respectively by the following formulas B-1 to B-4:

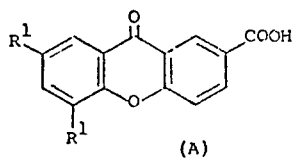
(A)

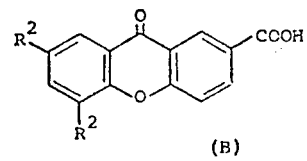
(B)

and the pharmaceutically acceptable, non-toxic esters, amides, and salts thereof:

wherein the $R^1$ groups are identical and selected from 1-hydroxylower alkyl and the lower alkyl, cycloalkyl, tetrahydrofuran-2-yl, tetrahydropyran-2-yl, tetrahydropyran-4-yl and 4-alkoxytetrahydropyran-4-yl ethers thereof and the carboxylic acyl esters thereof; lower alkanoyl; and the group $$-\underset{R}{S(O)_n}$$

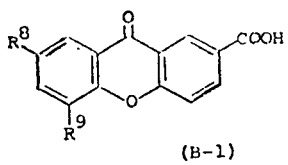
(B-1)

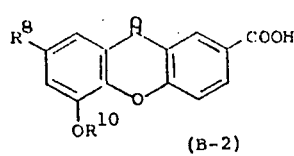
(B-2)

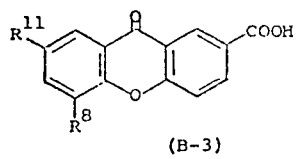
(B-3)

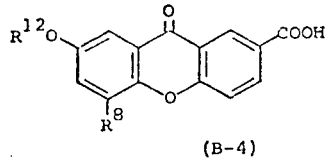
(B-4)

and the pharmaceutically acceptable, non-toxic esters, amides, and salts thereof; wherein $R^8$ is as defined above, and each of $R^9$, $R^{10}$, $R^{11}$, and $R^{12}$ is alkyl.

In a second aspect, the present invention is directed to a method useful for relieving symptoms associated with allergic manifestations such as are brought about by antigenantibody (allergic) reactions. In the relief of these symptoms, the method hereof serves to inhibit the effects of the allergic reaction when administered in an effective amount. While not intending to be bound by any theoretical mechanism of action, the method hereof is believed to operate by inhibiting the release and/or the action of toxic products, e.g. histamine, 5-hydroxytryptamine, slow releasing substance (SRS-A), and others, which are produced as a result of a combination of specific antibody and antigen (allergic reaction). These properties make the subject compounds particularly useful in the treatment of various allergic conditions.

The compounds of the present invention are also smooth muscle relaxants, e.g. bronchial dilaters, and are therefore useful in the treatment of conditions in which such agents may be indicated, as for instance, in the treatment of bronchoconstriction. The compounds of the present invention are also vasodilators and are therefore useful in the treatment of conditions in which such agents may be indicated, as for instance, in renal and cardiac disorders.

This aspect of the present invention thus relates to a method useful for inhibiting the effects of the allergic reaction which comprises administering an effective amount of a compound selected from those represented by the following formulas:

in which n is the integer 1 or 2, R is lower alkyl when n is 1 and R is lower alkyl, hydroxy, amino, monolower alkylamino, or dilower alkylamino when n is 2; and one $R^2$ group is selected from alkyl and alkoxy and the other $R^2$ group is selected from 1-hydroxylower alkyl and the lower alkyl, cycloalkyl, tetrahydrofuran-2-yl, tetrahydropyran-2-yl, tetrahydropyran-4-yl and 4-alkoxytetrahydropyran-4-yl ethers thereof and the carboxylic acyl esters thereof; lower alkanoyl, and the group $$-\underset{R}{S(O)_n}$$

in which each of n and R is as defined above; or a pharmaceutically acceptable non-toxic composition incorporating said acids, esters, amides or salts as an essential ingredient.

The present invention, in a third aspect, is directed to pharmaceutical compositions useful for inhibiting the effects of the allergic reaction comprising an effective amount of a compound selected from those represented by the following formulas:

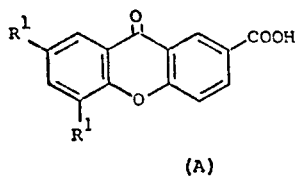
(A)

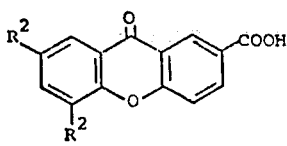
(B)

and the pharmaceutically acceptable, non-toxic esters, amides, and salts thereof;

wherein $R^1$ groups are identical and selected from 1-hydroxylower alkyl and the lower alkyl, cycloalkyl, tetrahydrofuran-2-yl, tetrahydropyran-2-yl, tetrahydropyran-4-yl and 4-alkoxytetrahydropyran-4-yl ehters thereof and the carboxylic acyl esters thereof; lower alkanoyl, and the group

in which $n$ is the integer 1 or 2, R is lower alkyl when $n$ is 1 and R is lower alkyl, hydroxy, amino monolower alkylamino, or dilower alkylamino when $n$ is 2; and one $R^2$ group is selected from alkyl and alkoxy and the other $R^2$ group is selected from 1-hydroxylower alkyl and the lower alkyl, cycloalkyl, tetrahydrofuran-2-yl, tetrahydropyran-2-yl, tetrahydropyran-4-yl and 4-alkoxytetrahydropyran-4-yl ethers thereof and the carboxylic acyl esters thereof; lower alkanoyl, and the group

in which each of $n$ and R is as defined above; in admixture with a pharmaceutically acceptable non-toxic carrier.

In the practice of the method of the present invention, an effective amount of a compound of the present invention or pharmaceutical compositions thereof, as defined above, is administered via any of the usual and acceptable methods known in the art, either singly or in combination with another compound or compounds of the present invention or other pharmaceutical agents, such as antibiotics, hormonal agents, and so forth. These compounds or compositions can thus be administered orally, topically, parenterally, or by inhalation and in the form of either solid, liquid, or gaseous dosages including tablets, suspensions, and aerosols, as discussed in more detail hereinafter. The administration can be conducted in single unit dosage form with continuous therapy or in single dose therapy ad libitum. In the preferred embodiments, the method of the present invention is practiced when relief of symptoms is specifically required, or, perhaps, imminent; however, the method hereof is also usefully practiced as continuous or prophylactic treatment.

In view of the foregoing as well as in consideration of the degree or severity of the condition being treated, age of subject, and so forth, all of which factors being determinable by routine experimentation by one skilled in the art; the effective dosage in accordance herewith can vary over a wide range. Generally, an effective amount ranges from about 0.005 to about 100 mg. per kg. of body weight per day and preferably from about 0.01 to about 100 mg. per kg. of body weight per day. In alternate terms, an effective amount in accordance herewith generally ranges from about 0.5 to about 7000 mg. per day per subject.

Useful pharmaceutical carriers for the preparation of the compositions hereof, can be solids, liquids, or gases. Thus, the compositions can take the form of tablets, pills, capsules, powders, sustained release formulations, solutions, suspensions, elixirs aerosols, and the like. The carriers can be selected from the various oils including those of petroleum, animal, vegetable, or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water, ethanol, and the like. Suitable pharmaceutical carriers and their formulation are described in "Remingtons Pharmaceutical Sciences" by E. W. Martin. Such compositions will, in any event, contain an effective amount of the active compound together with a suitable amount of carrier so as to prepare the proper dosage form for proper administration to the host.

The compounds of the present invention demonstrate activity as inhibitors of the effects of the allergic reaction as measured by tests indicative of such activity involving passive cutaneous anaphylaxis as substantially described, for example, by J. Goose et al., *Immunology*, 16, 749 (1969).

Certain of the compounds of the present invention can be prepared in accordance with the following reaction sequence:

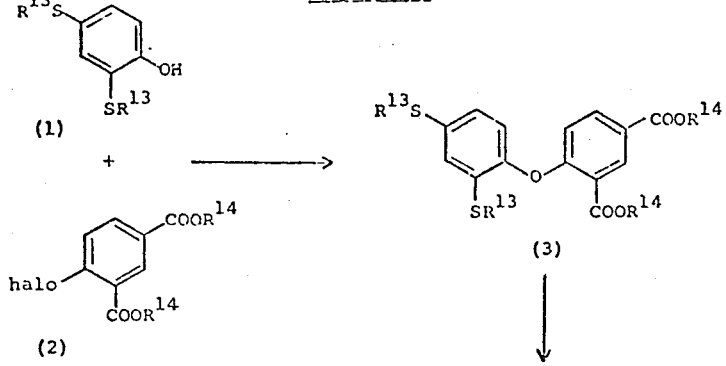

Sequence A

-continued

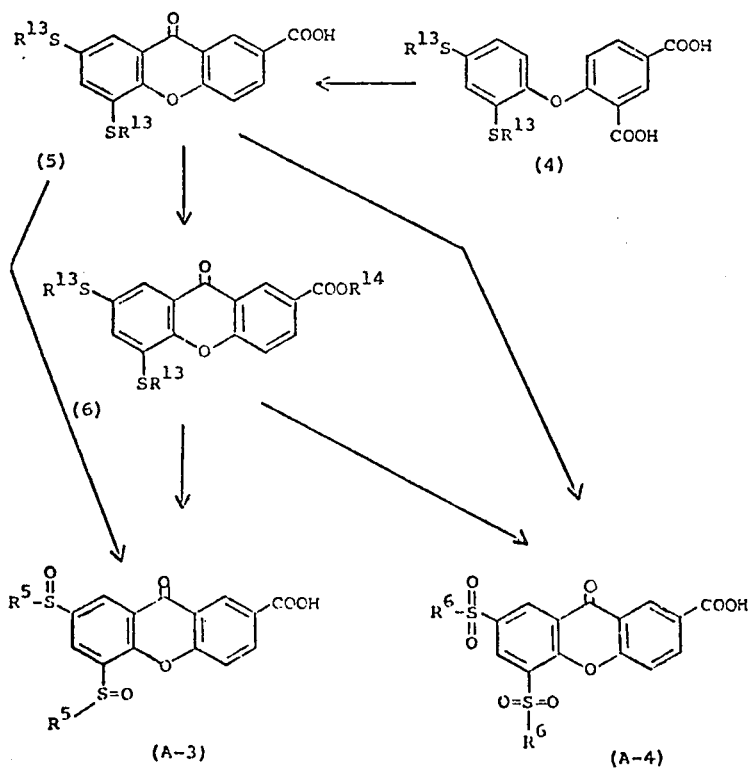

wherein each of $R^5$ and $R^6$ is as above defined; halo is bromo, chloro, fluoro, or iodo, preferably bromo; and each of $R^{13}$ and $R^{14}$ is lower alkyl, $R^{14}$ being preferably methyl.

With reference to the above reaction sequence, an ortho, para disubstituted ($SR^{13}$) phenol (1) is condensed with the 1,3-dicarbo(lower)alkoxy-4-halobenzene compound (2) in the presence of cuprous oxide optionally in organic liquid reaction medium, preferably an organic amide such as dimethyl acetamide, dimethylformamide, N-methylpyrrolidone, tetramethylurea, and so forth, to prepare the corresponding 1,3-dicarbo(lower)alkoxy-4-(o,p-di-substituted phenyloxy)-benzene compound (3).

The reaction is preferably conducted in an inert organic reaction medium, such as those listed above, or suitable mixtures of one or more of such media. The reaction is further conducted at temperatures ranging from about 80° to about 220°C, preferably from about 120° to 200°C, and for a period of time sufficient to complete the reaction, ranging from about 2 hours to about 24 hours.

The reaction consumes the reactants on the basis of one mole of the substituted phenol per mole of the dicarbo(lower)-carboxyhalobenzene per half mole of cuprous oxide. However, the amounts of the reactants to be employed are not critical, some of the desired compound (3) being obtained when employing any proportions thereof. In the preferred embodiments, the reaction is conducted by reacting from about one to about three moles of the substituted phenol compound with about from one to about 1.2 moles of the dicarbo(lower)carboxyhalobenzene compound in the presence of from about 0.5 to about 0.6 moles of the cuprous oxide. The inert organic reaction medium, if employed, is used in solvent amounts.

Thereafter, the prepared compound (3) is base hydrolyzed to give the corresponding 1,3-dicarboxy-4-(o,p-di-substituted phenyloxy)-benzene (4). The base hydrolysis conditions can be any employed conventionally in the art. Generally, the hydrolysis reaction is conducted using an alkali metal hydroxide at about 50° to about 90°C and for a period of time sufficient to complete the reaction, ranging from about 15 minutes to about 60 minutes, preferably in the presence of inert organic reaction media such as those normally employed in organic chemical reactions of this type, e.g. aqueous alkanol solutions. Although two moles of base are required per mole of compound (3), the amounts employed are not critical to produce the desired hydrolysis. Preferably from about three to about five moles of base are employed per mole of compound (3) and the reaction media, if employed, is used in solvent amounts.

The thus prepared diacid compound (4) is then cyclized with phosphoryl chloride, thionyl chloride, sulfuric acid, hydrogen fluoride, or, preferably, polyphosphoric acid (PPA), to give the corresponding 5,7-disubstituted xanthone-2-carboxylic acid compound (5). The reaction is preferably, but optionally, conducted in an inert organic reaction medium including those usually employed in organic chemical reactions, such as dimethylsulfoxide, sulfolane, benzene, toluene, and so forth. The reaction is further conducted at temperatures ranging from about 60° to about 180°C, and for a period of time sufficient to complete the reaction ranging from about 15 minutes to about 90 minutes.

Although the reaction consumes the reactants on the basis of the mole of compound (4) per mole of cyclizing reagent, the reaction can be performed using any proportions of reactants. In the preferred embodiments, however, the reaction is conducted using from about 20 to about 50 moles of the cyclizing reagent per mole of starting compound (4).

The 5,7-di(lower alkylthio)xanthone-2-carboxylic acid compounds (5) thus prepared are then esterified (R$^{14}$) to give compounds (6) and the latter are oxidized followed by ester hydrolysis or compounds (5) are oxidized to give the 5,7-di-(lower alkylsulfinyl)- and 5,7-di(lower alkylsulfonyl)xanthono-2-carboxylic acid compounds (A-3) and (A-4).

The esterification (5 → 6) is conducted with ethereal diazoalkane or with a lower alkanol in the presence of a trace of sulfuric acid at reflux. Hydrolysis of the esters, if necessary, is conducted as described above for the conversion of compounds 3 → 4.

The oxidation of compounds 5 or 6 when conducted with a peracid, such as peracetic acid, m-chloroperbenzoic acid, p-nitroperbenzoic acid, perphthalic acid, and so forth, yields the corresponding 5,7-di(lower alkylsulfinyl) acid compounds (A-3). The oxidation is preferably conducted in liquid reaction media such as a chlorinated hydrocarbon, e.g. chloroform, methylene chloride, and carbon tetrachloride. The reaction is conducted at temperatures ranging from about −10° to about 60°C, preferably from about 0° to about 30°C and for a period of time sufficient to complete the reaction, ranging from about 1 hour to about 6 hours. In the preferred embodiments, the reaction is conducted by reaction with from about 1 to about 1.1 moles of peracid.

Alternatively, the oxidation of compounds 5 or 6 with excess hydrogen peroxide gives the 5,7-di(lower alkylsulfonyl) acid compounds (A-4). The peroxide oxidation is preferably conducted in liquid reaction media such as a lower carboxylic acid, e.g. acetic acid and propionic acid. The reaction is further conducted at tempertures ranging from about 20° to about 100°C, preferably from 80° to about 90°C and for a period of time sufficient to complete the reaction, ranging from about 30 minutes to about 3 hours. In the preferred embodiments, the reaction is conducted by reaction of from about five to about ten moles of hydrogen peroxide per mole of starting compound.

In said oxidation steps, and particularly that employing peracid, a mixture of products (A-3) and (A-4) may be obtained. If obtained, the mixture can be conventionally separated, such as via chromatography, if desired, to isolate the respective oxidized products.

Certain of the compounds of the present invention can be prepared in accordance with the following reaction sequence:

Sequence B

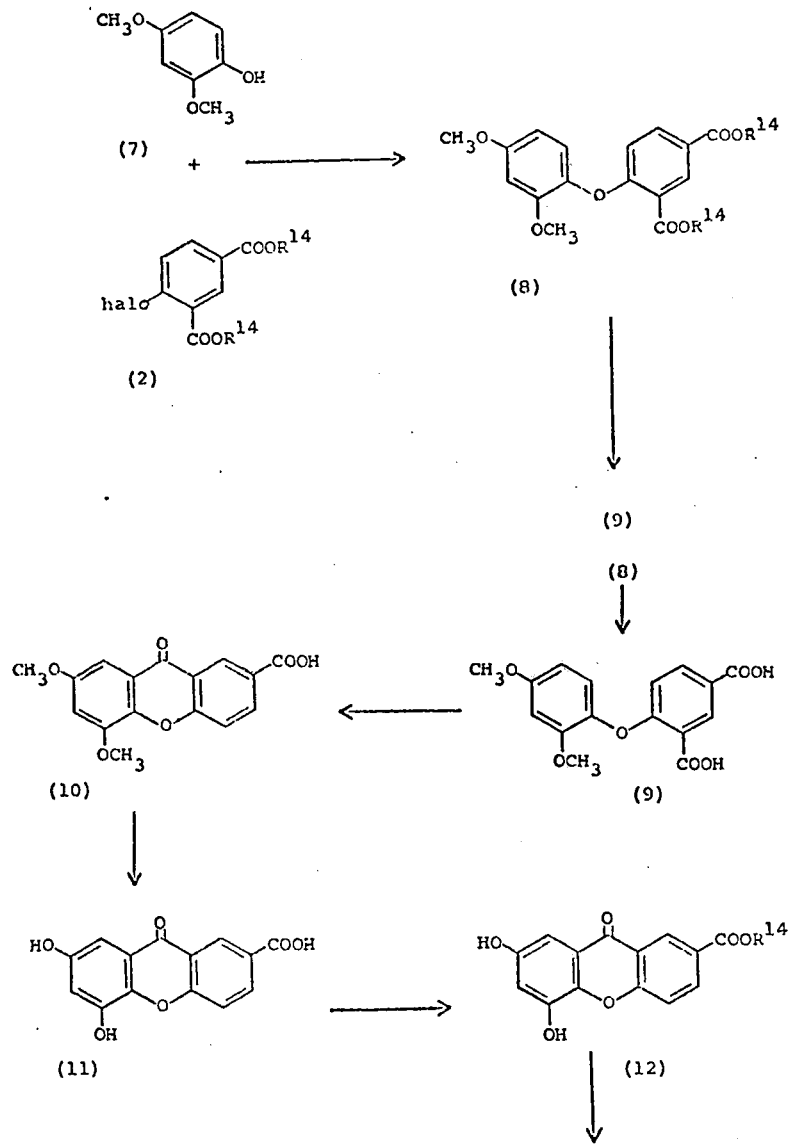

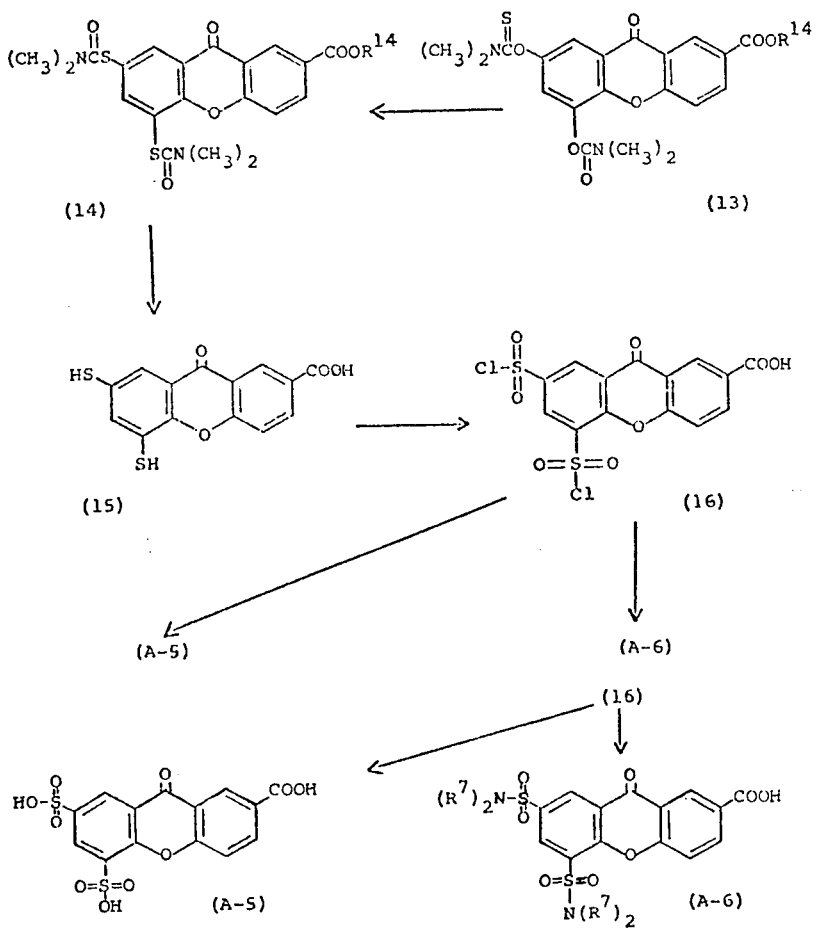

wherein each of halo, $R^7$ and $R^{14}$ is as above defined.

With reference to the above reaction sequence, the 5,7-dihydroxyxanthone-2-carboxylic acid esters (12) are prepared as described above in Sequence A for compounds 1 — 6 including the step (10 — 11) of hydrolyzing the methyl ethers with hydrobromic or hydroiodic acid and acetic acid, preferably at temperatures of from about 100° to about 160°C. Thereafter, compounds (12) are treated with a dialkylthiocarbamoyl chloride, such as dimethylthiocarbamoyl chloride, in the presence of base, such as an alkali metal hydride, and in organic liquid reaction media, preferably an organic amide such as those listed above with respect to reaction (1 + 2 — 3) to afford the products (13). the reaction is conducted at temperatures ranging from about 20° to about 100°C, preferably from about 60° to about 80°C and for a period of time sufficient to complete the reaction, ranging from about 1 hour to about 6 hours. In the preferred embodiments, the reaction is conducted by reaction of from about 2.2 to about 3.0 moles of dialkylthiocarbamoyl chloride per mole of compound (12).

The product compounds (13) are then rearranged by reaction at a temperature of from about 200° to about 250°C, preferably from about 220° to about 230°C, and for a period of time ranging from about 1 hour to about 8 hours and in the presence of organic medium such as sulfolane, nitrobenzene, triethyleneglycol, and so forth, which is preferably employed in solvent amounts, to give compounds (14).

Compounds (14) are then converted to the corresponding 5,7-dimercapto acid compounds (15) by base hydrolysis such as those described above for the preparation of compounds (4) from (3).

Compounds (15) are treated with excess chlorine under acidic conditions to afford compounds (16). This reaction is conducted employing a pH of about 1 by use of hydrochloric acid, optionally in acetic acid solution. The reaction is further conducted at temperatures ranging from about 20° to about 100°C, preferably from 50° to about 60°C and for a period of time sufficient to complete the reaction, ranging from about 2 hours to about 12 hours.

Compound (16) is then reacted with a base, such as alkali metal hydroxide, preferably under aqueous conditions and at a temperature ranging from about 20° to about 100°C, preferably from 80° to about 90°C and for a period of from about 1 hour to about 2 hours and acidified to give the 5,7-di-sulfo-substituted acid compounds (A-5).

Compounds (16) can be treated with ammonia, monolower alkylamine, or dilower alkylamine to give the 5,7-disulfamoyl, di(monolower alkyl)sulfamoyl, and -di(dilower alkyl)sulfamoyl acid compounds (A-6). this reaction is conducted at temperatures ranging from about 0° to about 80°C, preferably from 20° to about 30°C, and for a period of time sufficient to complete the reaction, ranging from about 1 hour to about 8 hours. In the preferred embodiments, the reaction is conducted by reaction of from about 10 to about 20 moles of amine per mole of compound (16). This reaction is further conducted in organic reaction media such as those described above, preferably tetrahydrofuran, dioxane, dimethylsulfoxide, and so forth.

The C-5,7 di(chlorosulfonyl)xanthone-2-carboxylic acid compound (16) is a novel intermediate useful as described above.

Certain of the compounds of the present invention can be prepared in accordance with the following reaction sequence:

With reference to the above reaction sequence, the 5,7-dialkylxanthone-2-carboxylic acid compounds (20) are prepared as described above in Sequence A for compounds 1 → 6. Thereafter, compounds (20) are oxidized with chromic oxide in acetic acid, acetic anhydride to give the 5,7-di(loweralkanoyl) compounds (A-2) which can be reduced to the 5,7-di-(1-hydroxyloweralkyl) compound (A-1) with sodium borohydride.

Certain of the compounds of the present invention

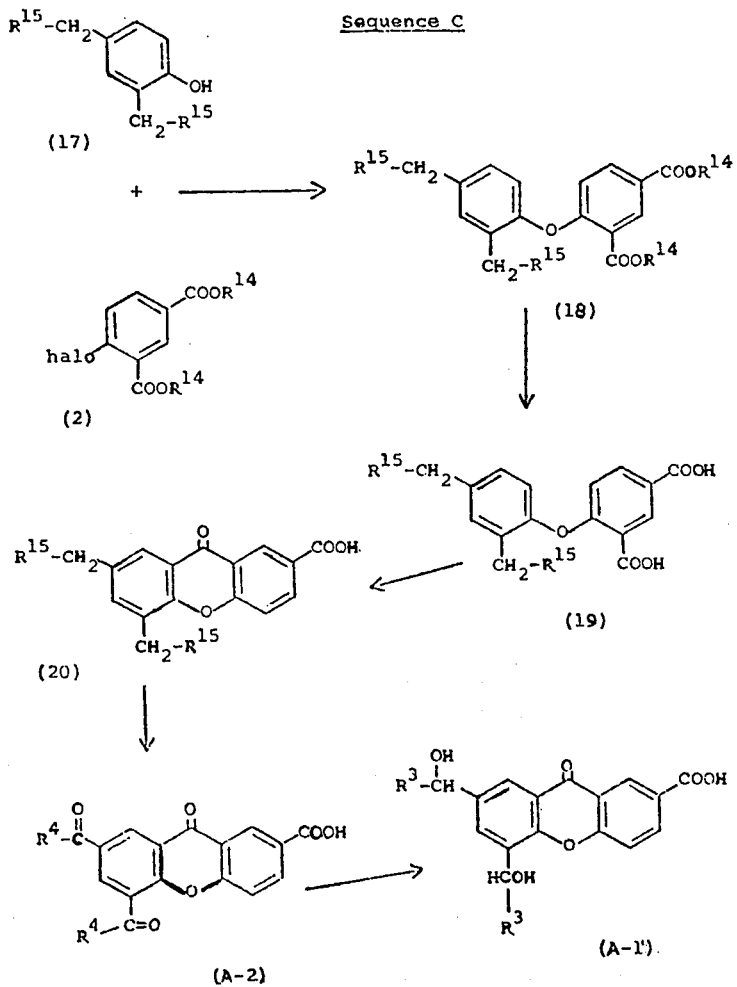

wherein each of halo, $R^{14}$, $R^3$, and $R^4$ is as above defined and $R^{15}$ is lower alkyl.

can be prepared in accordance with the following reaction sequence:

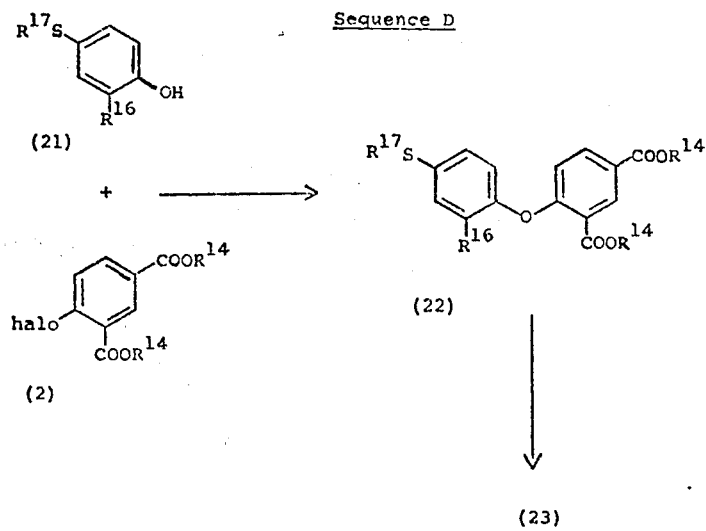

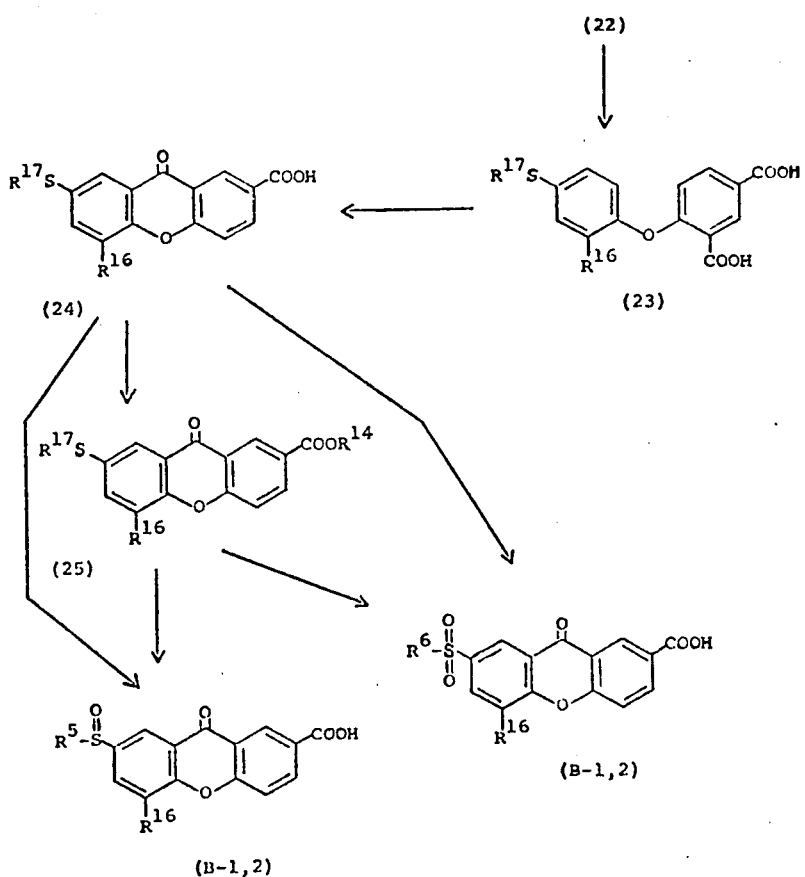
wherein each of halo, $R^{14}$, $R^5$, and $R^6$ is as above defined; $R^{16}$ is alkyl or alkoxy; and $R^{17}$ is lower alkyl.
Certain of the compounds of the present invention can be prepared in accordance with the following reaction sequence:
Sequence E
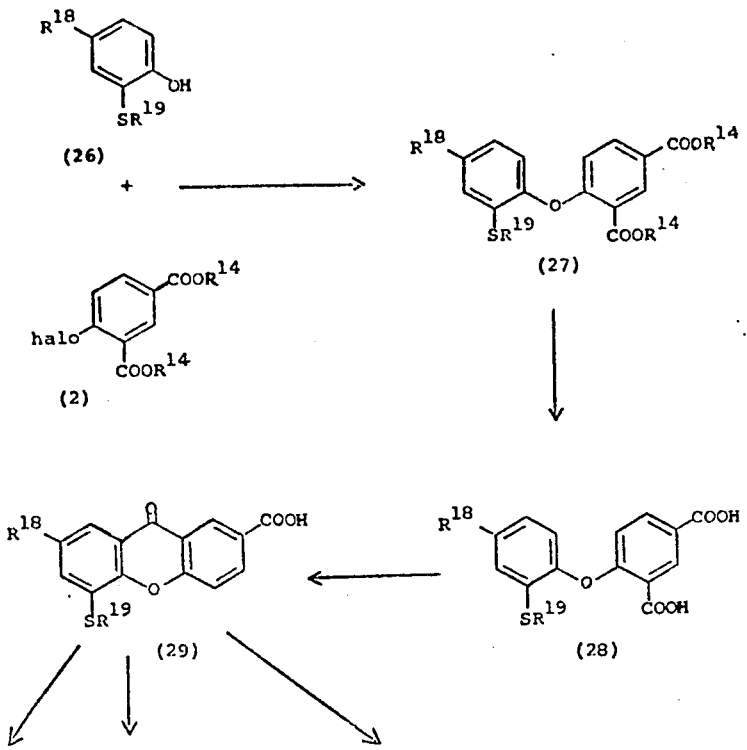

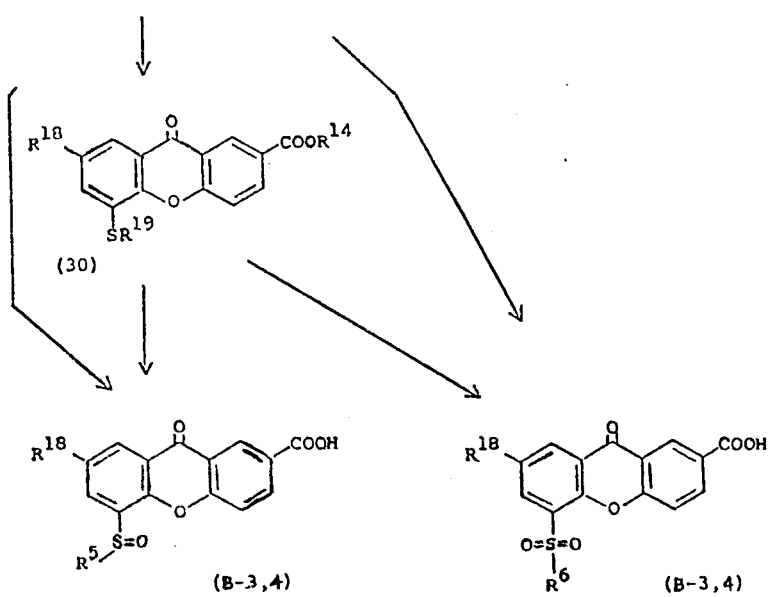

wherein each of halo, $R^{14}$, $R^5$, and $R^6$ is as above defined, $R^{18}$ is alkyl or alkoxy; and $R^{19}$ is lower alkyl.

With reference to the above reaction sequences D and E, the 5-alkyl or alkoxy-7-lower alkylthio compounds (24) and corresponding 5-lower alkylthio-7-alkyl or alkoxy compounds (29) are prepared as described above in Sequence A for compounds 1 → 6. Thereafter, the respective products are oxidized to the sulfinyl and sulfonyl compounds (B-1,2) and (B-3,4) either directly or through the acid esters (25) and (30), and as described above for compounds 5 ↔ 6 → A-3 and A-4.

SEQUENCE D'

Alternatively, the compounds of formula (24) wherein $R^{16}$ is the methoxy group are converted to the compounds of formulas (B'-2) in accordance with the following reaction sequence:

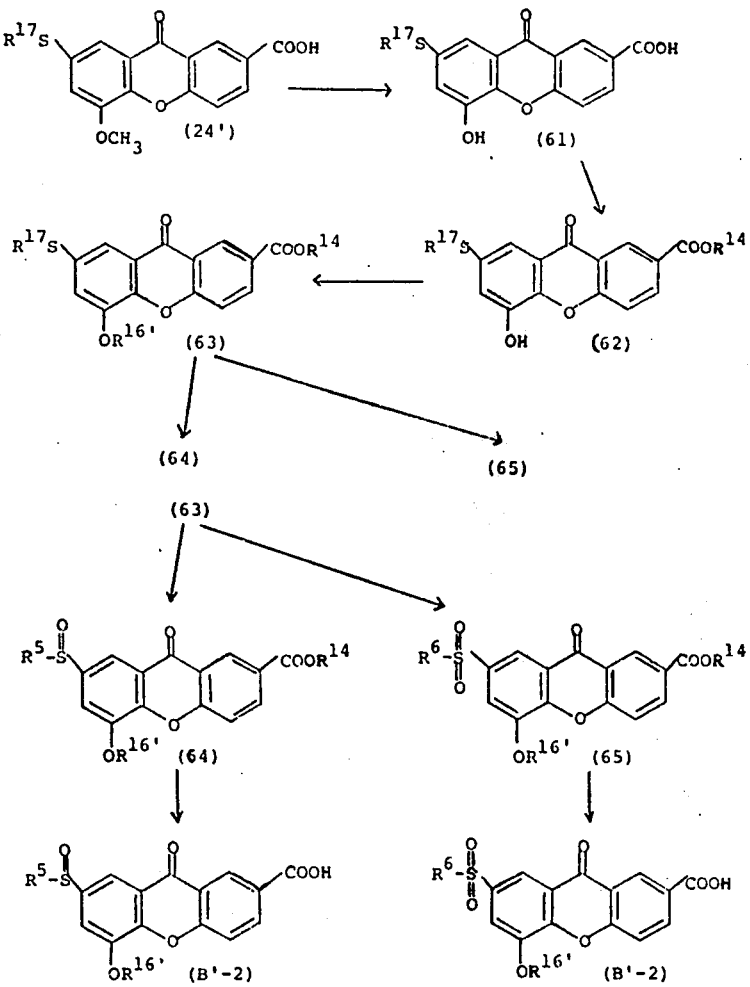

wherein each of $R^{17}$, $R^{14}$, $R^5$ and $R^6$ is as above defined; and $R^{16'}$ is a higher alkyl group containing from six to twelve carbon atoms.

SEQUENCE E

Alternatively, the compounds of formula (29) wherein $R^{18}$ is the methoxy group are converted to the compounds of formulas (B'-4) in accordance with the following reaction sequence:

esterified with an alkyl halide, e.g., methyl iodide, ethyl bromide, and the like, in the presence of an organic solvent, e.g., dimethylformamide, dimethylacetamide, n-methylpyrrolidone, and the like, and lithium carbonate, to obtain the ester compounds of formulas (62) and (67).

The 5-hydroxy-7-lower alkylthio ester compounds (62) and 5-lower alkylthio-7-hydroxy ester compounds (67) are etherified with a higher alkyl halide, preferably a higher alkyl bromide, e.g., 1-bromohexane

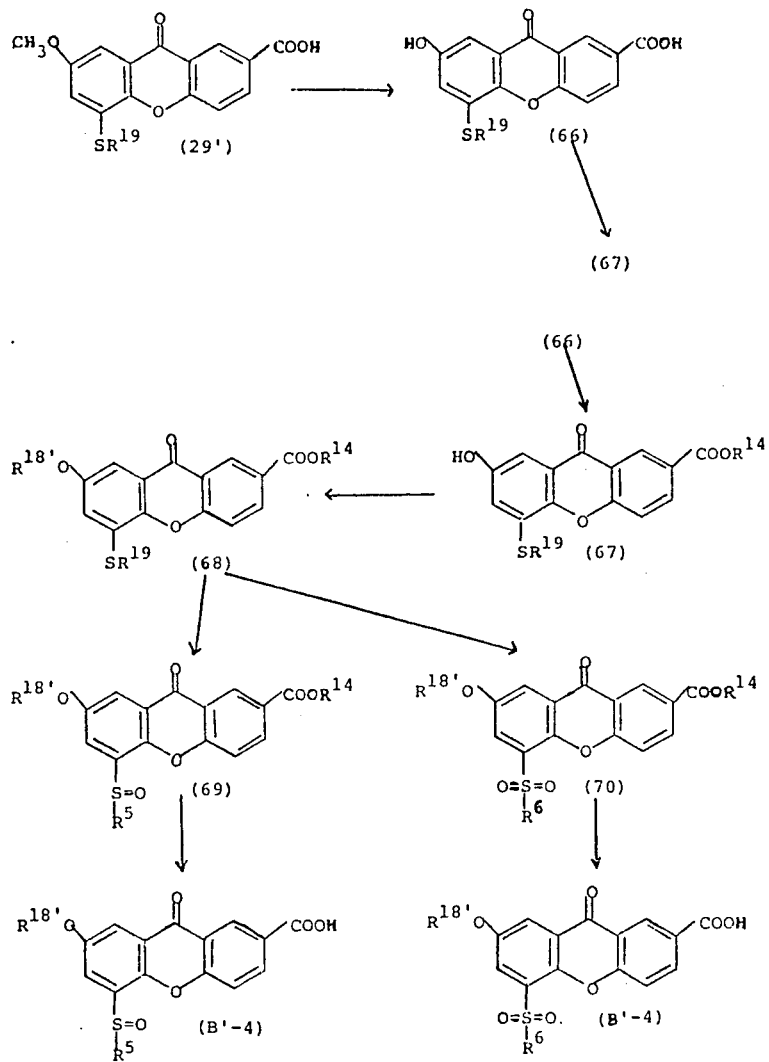

wherein each of $R^{19}$, $R^{14}$, $R^5$ and $R^6$ is as above defined; and $R^{18'}$ is a higher alkyl group containing from six to twelve carbon atoms.

With reference to the above reaction sequences D' and E', the 5-methoxy-7-lower alkylthio compounds (24') and 5-lower alkylthio-7-methoxy compounds (29') are converted to their corresponding 5-hydroxy-7-lower alkylthio compounds (61) and 5-lower alkylthio-7-hydroxy compounds (66) by treatment with hydriodic or hydrobromic acid in the presence of a suitable solvent, e.g., acetic anhydride, acetic acid of propionic acid.

The compounds of formulas (61) and (66) are then (hexyl bromide), 1-bromoheptane (heptyl bromide), 2-bromoheptane, 1-bromoctane (octyl bromide), 1-bromododecane (dodecyl bromide), 2-bromododecane, and the like, in the presence of an organic solvent, e.g., dimethylformamide, dimethylacetamide, acetone, and the like, and potassium carbonate, to obtain the 5-higher alkoxy-7-lower alkylthio ester compounds (63) and 5-lower alkylthio-7-higher alkoxy ester compounds (68), respectively.

The compounds of formulas (63) and (68) are oxidized to the sulfinyl ester compounds of formulas (64) and (69), and sulfonyl ester compounds, formulas (65) and (70), as described above for the oxidation of the compounds of formula (6) to the compounds of formulas (A-3) and (A-4). The compounds of formulas (64) and (69) and (65) and (70) are then subjected to base hydrolysis, according to the method described above for the conversion of the compounds of formula (3) to the compounds of formula (4), thus yielding the 5-higher alkoxy-7-lower alkylsulfinyl acids of formula (B'-2) and 5-lower alkylsulfinyl-7-higher alkoxy acids of formula (B'-4) and 5-higher alkoxy-7-lower alkylsulfonyl acids of formula (B'-2) and 5-lower alkylsulfonyl-7-higher alkoxy acids of formula (B'-4).

Certain of the compounds of the present invention can be prepared in accordance with the following reaction sequence:

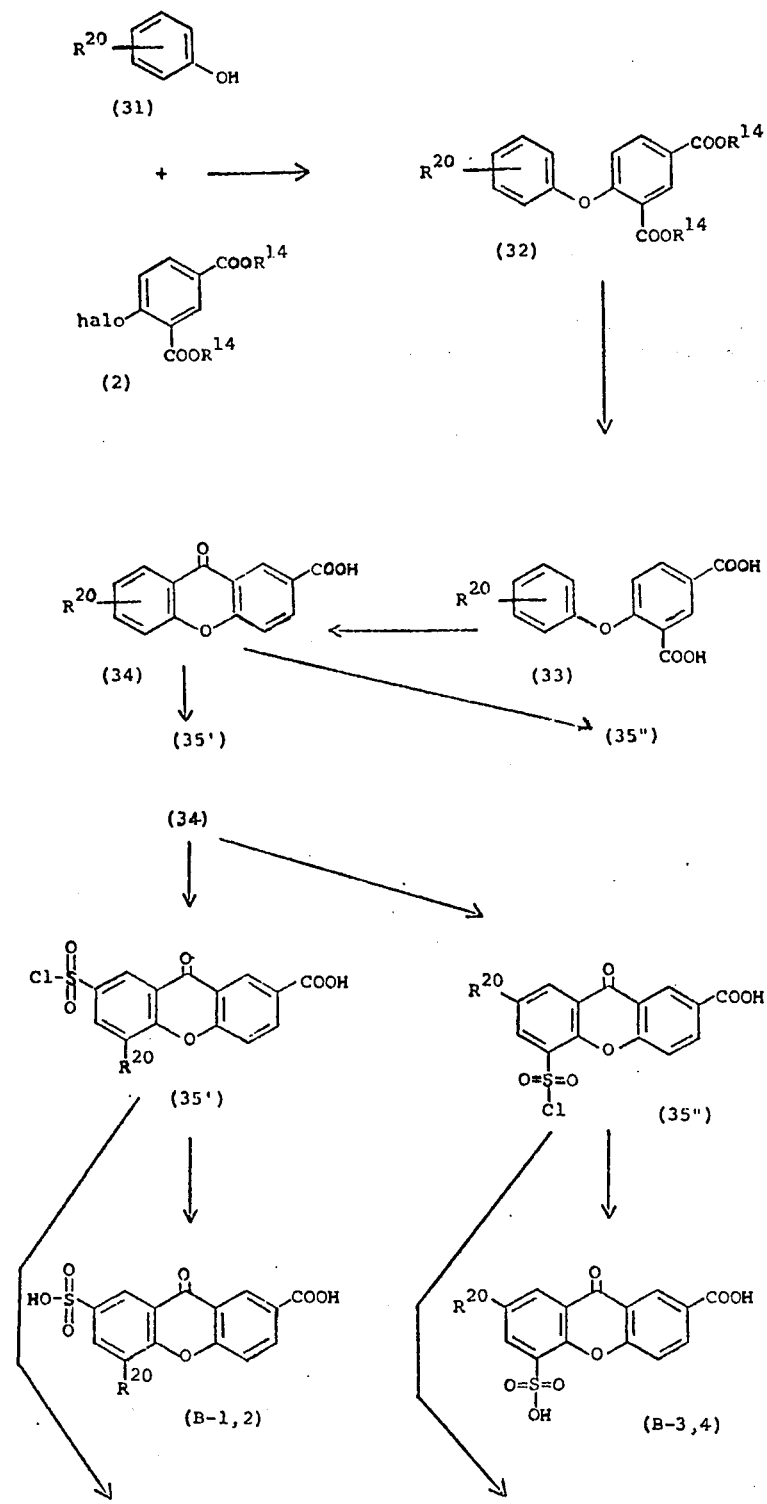

Sequence F

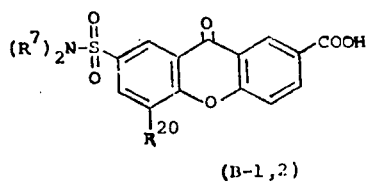

(B-1,2)

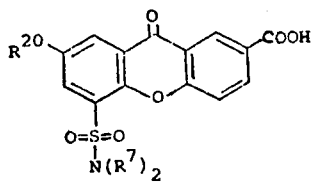

(B-3,4)

wherein each of halo, $R^{14}$ and $R^7$ is as defined above and $R^{20}$ is alkyl or alkoxy.

With reference to the above reaction sequence, the 5- or 7-alkyl or alkoxy compounds (34) are prepared as described above in Sequence A for compounds 1 6. Thereafter the 5- or 7-chlorosulfonyl compounds (35') and (35'') are prepared by treating (34) with chlorosulfonic acid. This reaction is conveniently conducted in excess reagent at from about 100° to about 150°C and for a period of from about 2 to 4 hours. In the preferred embodiments, amounts of chlorosulfonic acid ranging from about 10 to about 25 moles per mole of starting compound are employed.

Thereafter, compounds (35') and (35'') are converted to the sulfo compounds (B-1, 2) or the sulfamoyl compounds (B-3, 4), such as described above for the preparation of compounds (A-5) and (A-6).

Certain of the compounds of the present invention can be prepared in accordance with the following reaction sequence:

Sequence G

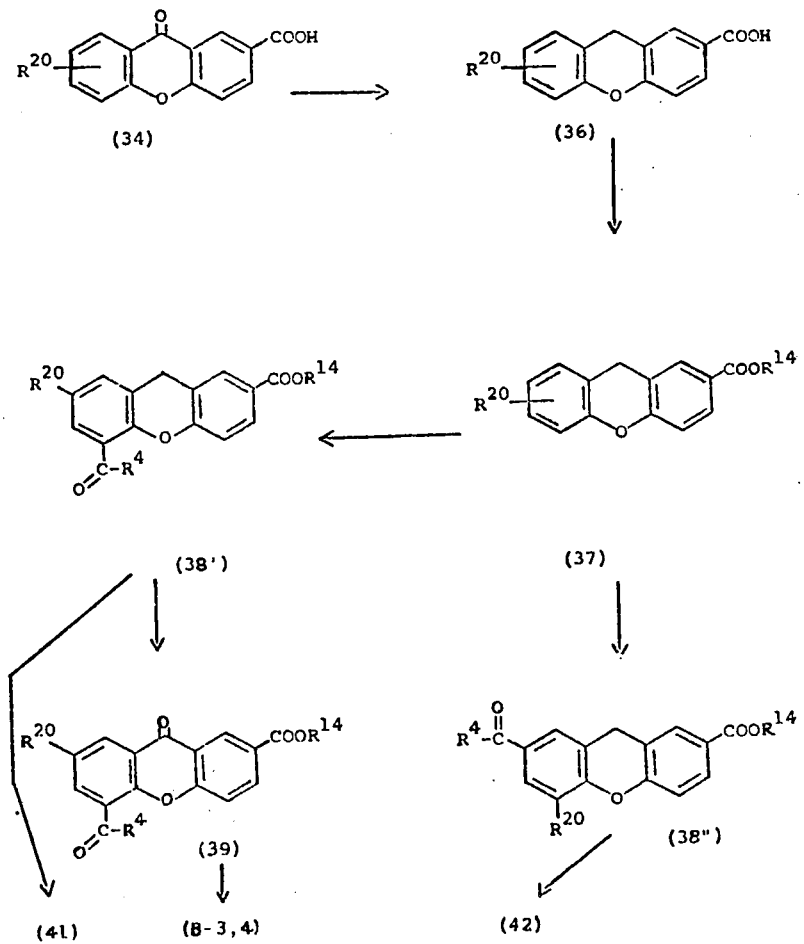

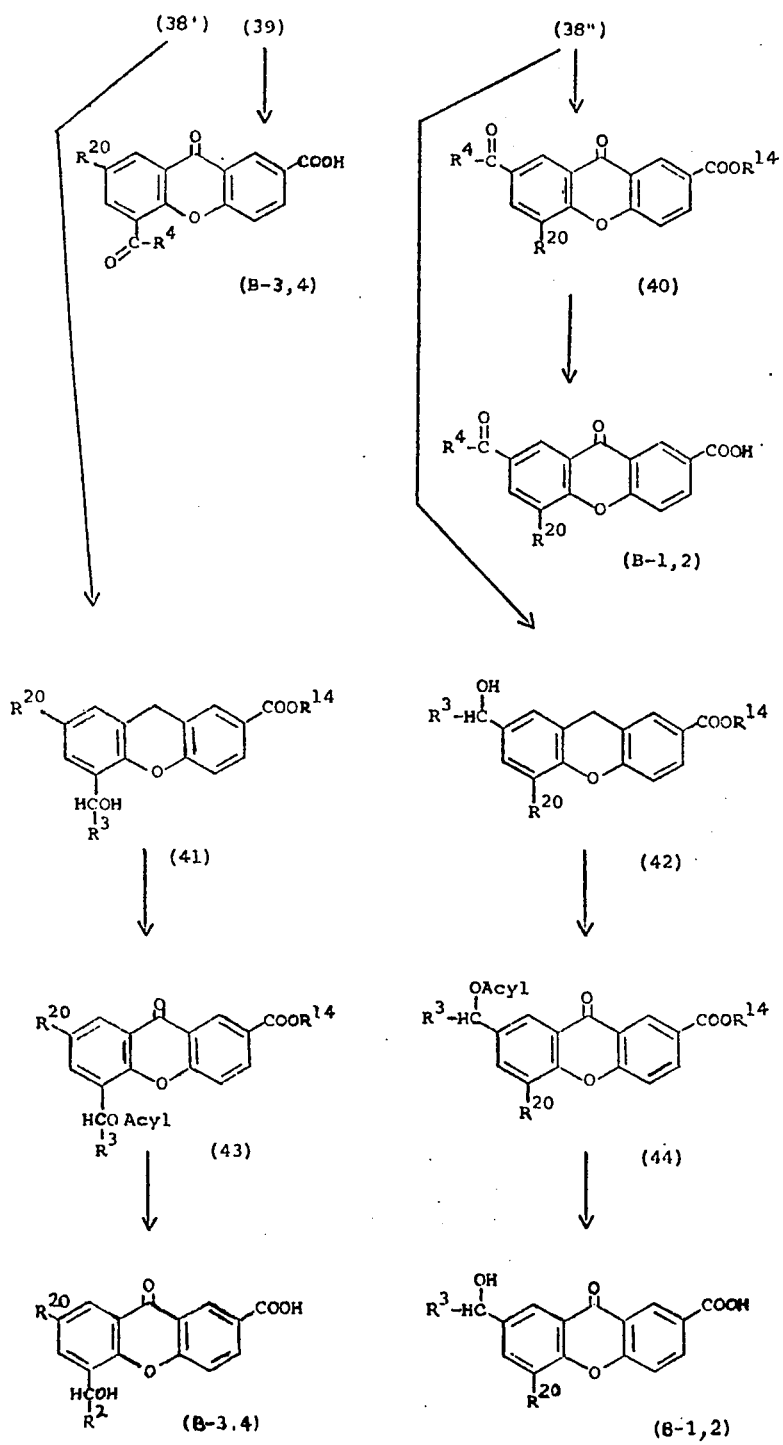

wherein each of halo, $R^{14}$, $R^{20}$, $R^3$, and $R^4$ is as above defined, and Acyl is lower alkanoyl, preferably acetyl.

With respect to the above reaction sequence, compound (34) is prepared as described in Sequence F. Thereafter the 9-oxo group is reduced such as with potassium hydroxide in hydrazine, zinc and potassium hydroxide in ethanol, and the like, to prepare the corresponding C-5 or 7 substituted xanthene-2-carboxylic acid (36). This compound is esterified ($R^{14}$) as described above and the ester (37) then acylated with a lower alkanoyl chloride in the presence of aluminum chloride to give the corresponding 5- or 7-lower alkanoyl compounds (38' and 38").

The compounds of formula (38' or 38") are reduced, such as with sodium borohydride, to prepare the corresponding 1-hydroxy-lower alkyl compounds (41 and 42) which are acylated via conventional techniques and the acylated compounds are oxidized under Jones conditions to prepare the corresponding 5- or 7-(1-acyloxy-lower alkyl) xanthone-2-carboxylic acid esters (43 and 44) which, when hydrolyzed under base conditions, gives the corresponding 5- or 7-(1-hydroxylower alkyl) xanthone-2-carboxylic acids (B-1,2 and B-3,4).

Compounds (38' and 38'') can be oxidized, such as via the Jones oxidation, to give (39 and 40) which are hydrolyzed to give the 5- or 7-lower alkanoylxanthone-2-carboxylic acids (B-1,2 and B-3,4).

Further methods by which certain of the compounds of the present invention can be prepared are as set forth in the following reaction sequences (H to K):

Sequence H

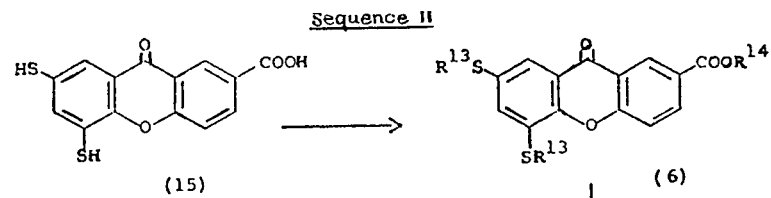

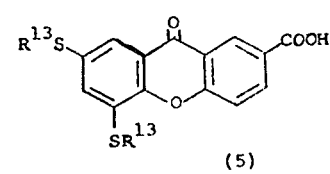

Sequence I

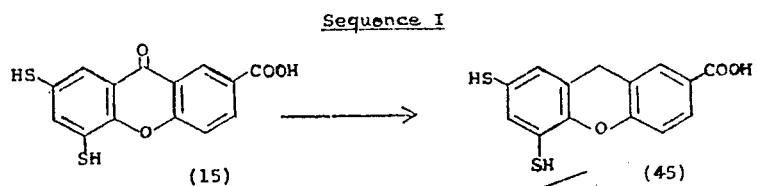

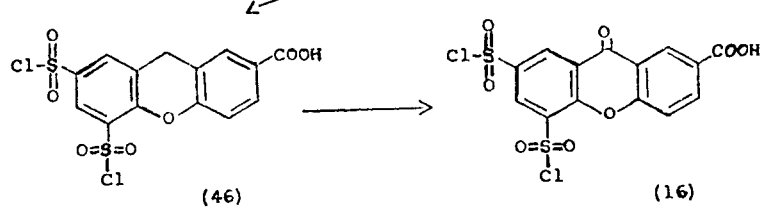

Sequence J

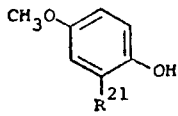

(47)

+

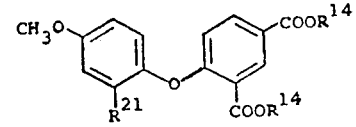

(48)

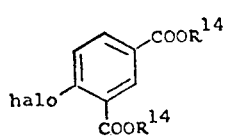

(2)

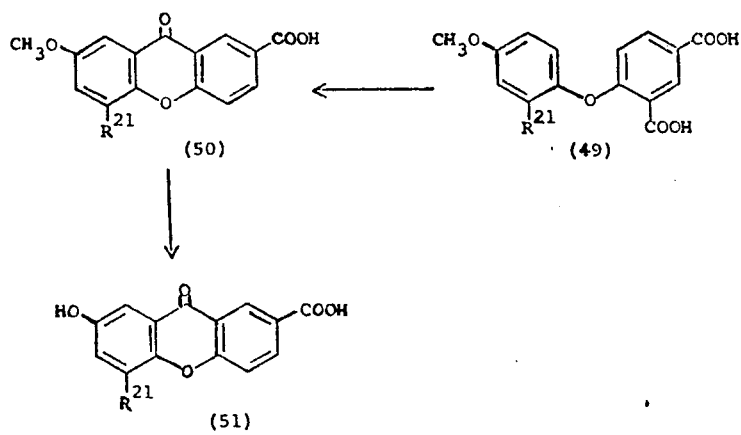

Sequence K

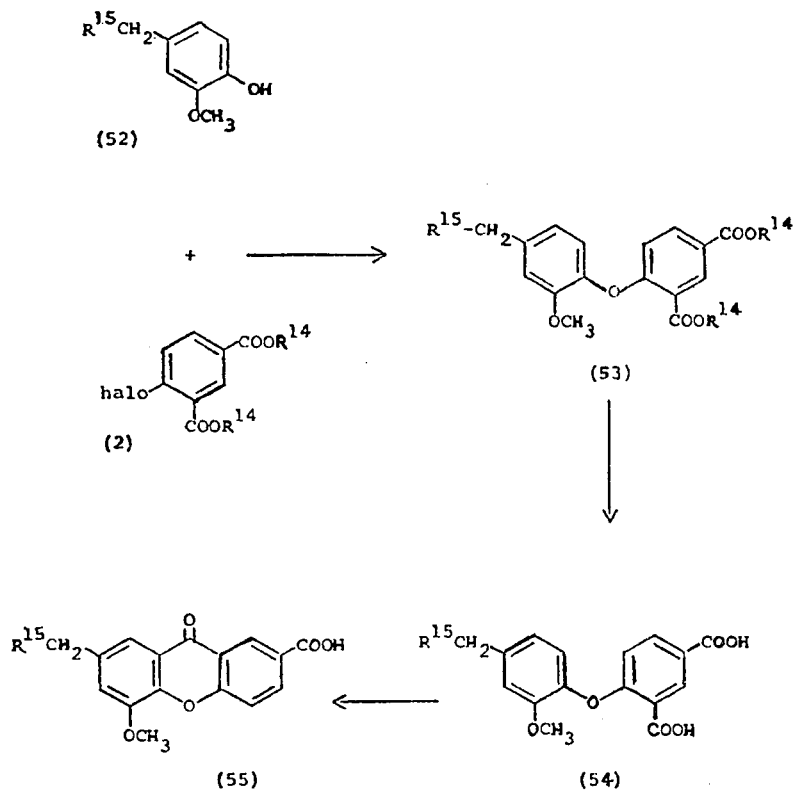

wherein each of $R^{13}$, $R^{14}$, $R^{15}$, and halo is as above defined and $R^{21}$ is alkyl.

With reference to the above reaction sequences, Sequence H provides an alternate method by which compounds (5), useful as described in Sequence A, are prepared from compound (15) of Sequence B. Sequence I provides an alternate method by which compounds (16), useful as described in Sequence B, are prepared from compound (15) of Sequence B through the xanthene sequence as described in Sequence C. Sequence J provides a method for preparing the 5-lower alkyl-7-hydroxy compounds (51) which are useful as described in Sequence B. Sequence J is also useful for preparing the corresponding 7-lower alkyl-5-hydroxy compounds, useful as described in Sequence B. Sequence K describes the preparation of the 5-methoxy-7-alkyl compounds (55) and is also useful for preparing the 5-alkyl-7-methoxy compounds, each of which is useful as described in Sequence C.

An alternative basic method by which certain of the compounds hereof can be prepared, as depicted above, is depicted as follows:

Sequence L

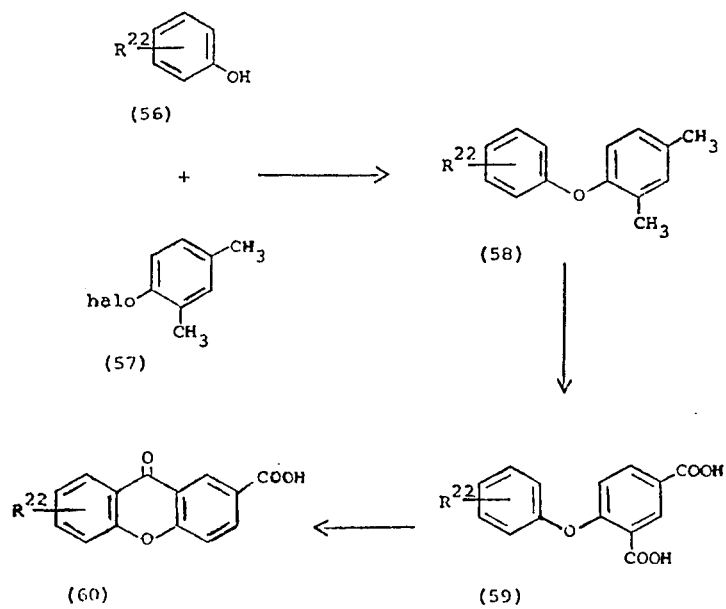

wherein halo is as above defined and $R^{22}$ at ortho or para or both positions is alkoxy.

With reference to Sequence L, an appropriate phenol (56) is treated with 1,3-dimethyl-4-halo- (preferably iodo) benzene (57), as described above, to prepare the corresponding 1,3-dimethyl-4-phenyloxybenzene (58). This compound is then oxidized such as with potassium permanganate in aqueous t-butanol to give (59). This compound is then cyclized, as described above, to give the corresponding xanthone-2-carboxylic acid (60) which can be treated variously as described above, to prepare certain of the compounds of the present invention.

The starting compounds for use in the present invention are known and can be prepared by processes known per se. Thus, the 1,3-dicarbo(lower)alkoxy-4-halobenzene starting compounds (2) are conveniently prepared by oxidizing 1,3-dimethyl-4-halo-benzene (4-halo-m-xylene) with potassium permanganate, as described above (58 → 59), followed by conventional esterification. The o,p-diloweralkylthiophenol compounds (1) are conveniently prepared by treating o-hydroxybenzoic acid with excess chloro-sulfonic acid to give the corresponding o-hydroxy-m,m-di(chlorosulfonyl)-benzoic acid. This is reduced to the corresponding dimercapto compound with zinc and hydrogen chloride in acetic acid. The resultant compound is dialkylated with lower alkyl halide and potassium carbonate in dimethylformamide or with dialkylsulfate in aqueous sodium hydroxide to give o-alkoxy-m,m-di(alkylthio)-benzoic acid. The latter is decarboxylated with heating in the presence of copper and quinoline and the resultant compound selectively hydrolyzed with pyridine hydrochloride or with hydrogen bromide in acetic acid to give the o,p-di(lower alkylthio)-phenol.

The o,p-dialkoxyphenol starting compounds, i.e. (7), are prepared by treating o,p-dihydroxyacetophenone with an appropriate alkyl halide and potassium carbonate in dimethylformamide to give the corresponding dialkoxy compound. The latter is treated under Baeyer-Villiger conditions with peracid, e.g. peracetic or m-chloroperbenzoic acid, in chloroform containing p-toluenesulfonic acid to give 1-acetoxy-2,4-dialkoxybenzene. The latter is hydrolyzed to give the o,p-diloweralkoxyphenol compounds.

The o,p-diloweralkoxyphenol starting compounds, i.e. (17), are prepared by treating 1,3-dialkylbenzene with acetyl chloride and aluminum chloride to give the corresponding acetyl compound followed by a Baeyer-Villiger reaction and hydrolysis or by treating 1,3-dialkylbenzene with nitric acid and sulfuric acid to give the 1-nitro-2,4-dialkylbenzene, reduction of the latter with stannous chloride to the amine, treatment thereof with sodium nitrite in HCl followed by treatment with dilute sulfuric acid and heat to give the o,p-dialkylphenols.

The o-alkyl or -alkoxy-p-alkylthiophenol starting compounds, i.e., (21) wherein the $R^{16}$ group contains from one to twelve carbon atoms, are conveniently prepared by treating an o-alkyl or -alkoxyphenol in which the alkyl or alkoxy group contains from one to twelve carbon atoms with chlorosulfonic acid in chloroform, followed by reduction with zinc — HCl in acetic acid, followed by alkylation, all as described above (cf. preparation of 1) or by treatment of an o-alkyl or -alkoxyphenol with dialkylsulfoxide and gaseous hydrogen chloride to give the corresponding 3-alkyl or -alkoxy-4-hydroxybenzene dialkylsulfoxide chloride. The latter is heated to give the corresponding o-alkyl or -alkoxy-p-alkylthiophenol product.

The o-alkylphenol used as the starting material in preparing the o-alkyl compounds of e.g. formula (21) is prepared by treating phenol with an alkanoyl chloride (e.g. n-octanoyl chloride) to obtain the corresponding phenyl alkanoate (e.g. phenyl n-octanoate) which is then treated with aluminum chloride at 150°C to obtain predominantly the c-alkanoyl phenol (e.g. o-n-octanoyl phenol) which is removed from any p-isomer which may be present by steam distillation. The o-alkanoyl phenol (e.g. o-n-octanoyl phenol) is then reduced with zinc amalgam-hydrochloric acid to obtain the o-alkyl phenol (e.g. o-n-octyl-phenol).

The corresponding o-alkylthio-p-alkyl or -alkoxyphenol starting compounds, i.e. (26) wherein the $R^{16}$ group contains from one to twelve carbon atoms, are prepared by treating a p-alkyl or -alkoxyphenol in which the alkyl or alkoxy group contains from one to twelve carbon atoms with chlorosulfonic acid, followed by reduction, alkylation, all as described above, provides the desired compounds.

The p-alkyl phenol used as the starting material in preparing the p-alkyl compounds of e.g. formula (26) is prepared by treating phenol with an alkanoyl chloride (e.g. n-octanoyl chloride) to obtain the corresponding phenyl alkanoate (e.g. phenyl n-octanoate) which is then treated with aluminum chloride at 25°C and in the presence of nitrobenzene to obtain predominantly p-alkanoyl phenol (e.g. p-n-octanoyl phenol) which is then purified by steam distillation to remove any o-isomer which may be present. The p-alkanoyl phenol (e.g. p-n-octanoyl phenol) is then reduced with zinc amalgam-hydrochloric acid to obtain the p-alkyl phenol (e.g. p-n-octyl phenol).

The o-alkyl-p-alkoxyphenol starting compound, i.e. (47), is prepared by treating 1-alkyl-3-alkoxybenzene under Friedel-Crafts conditions to give the corresponding acetyl compound followed by a Baeyer-villiger reaction and hydrolysis, all as described above. Alternatively, p-alkoxyphenol starting compounds can be acetylated ortho to the hydroxy group and the resultant compound reduced. The o-alkoxy-p-alkylphenol starting compounds are prepared from o-alkoxyphenols via p-acetylation and reduction, all as described above.

The carboxylic acyl esters of the secondary hydroxy alkyl substituted compounds (i.e. $R'$=carboxylic acyl and $R^8$=carboxylic acyl of 1-hydroxy alkyl) are prepared as described above or by secondary alcohol esterification methods known per se. One such method involves treating the 1-hydroxy alkyl products represented by Formulas A-1', B-1,2 and B-3,4 of Sequences C and G with aa carboxylic acid chloride or carboxylic acid anhydride in the presence of a base, preferably pyridine, at temperatures ranging from about 60° to about 90°C and for a period of time ranging from about 1 to about 2 hours to give the corresponding secondary carboxylic acyloxy alkyl substituted xanthone-2-carboxylic acid compound.

The alkyl and cycloalkyl ethers of the secondary hydroxyalkyl series ($R'$=alkyl, cycloalkyl and $R^8$=alkyl, cycloalkyl ethers of 1-hydroxy alkyl) are prepared by treatment of the xanthone acid ester with the appropriate alkyl- or cycloalkyl halide and sodium hydride in, e.g. dimethylformamide, followed by hydrolysis, as described above. The etherification reaction is conducted at from about 50° to about 80°C and for from about 1 to about 5 hours.

The t-butoxy ethers are prepared by treating the alcohol with isobutene in the presence of boron trifluoride and phosphoric acid in, e.g. methylene chloride, at temperatures of from about 10° to about 30°C and for from 10 to about 24 hours, or more, followed by hydrolysis of the acid ester group, as described above.

The tetrahydrofuran-2-yloxy and tetrahydropyran-2-yloxy ethers of the 1-hydroxyalkyl compounds are prepared by treatment with dihydrofuran or dihydropyran in the presence of p-toluenesulfonic acid and organic reaction medium, e.g. benzene, at about room temperature up to reflux, for from about two to about five days, followed by hydrolysis of the acid ester, as described above.

The 4-alkoxytetrahydropyran-4-yloxy ethers are prepared by treatment of the alcohol with 4-alkoxy-5,6-dihydro-2H-pyran, as described above for the preparation of the furanyl and pyranyl ethers, followed by acid ester hydrolysis. Treatment of the 4-alkoxytetrahydropyran-4-yloxy ether with aluminum chloride and lithium aluminum hydride in organic reaction medium affords the corresponding tetrahydropyran-4-yloxy ethers which are oxidized to give the corresponding ethers in the xanthone acid series. The latter can be directly prepared by treating the alcohol with 4-bromotetrahydropyran and base. See Harrison and Harrison, *Compendium of Organic Synthetic Methods*, Wiley-Interscience, New York (1971) 129 and the references cited thereon.

The acid esters of the xanthone-2-carboxylic acids hereof are prepared as described above (e.g. 5 → 6) upon treatment of the acid with ethereal diazoalkane such as diazomethane and diazoethane or with the desired lower alkyl iodide in the presence of lithium carbonate at room temperature or with the desired lower alkanol in the presence of a trace of sulfuric acid at reflux. The glycerol esters are prepared by treating the acid with thionyl chloride followed by treatment with a suitably protected ethylene glycol or propylene glycol (e.g. solketal) in pyridine, and hydrolyzing the protecting group of the ester thus formed with dilute acid. In the sulfo series, the carboxylic acid esters are preferably prepared with the desired lower alkanol in the absence of acid catalyst.

The amides of the xanthone-2-carboxylic acids hereof are prepared by treatment of the acids with thionyl chloride followed by treatment with anhydrous ammonia, alkyl, amine, dialkyl amine, dialkylaminoalkylamine, alkoxyalkylamine, or phenethylamine. In the lower alkyl sulfinyl series, the carboxylic acid amides are preferably prepared at the corresponding (lower alkylthio) stage followed by oxidation thereof, as described above.

The salts of the xanthone-2-carboxylic acids hereof are prepared by treating the corresponding acids with pharmaceutically acceptable base. Representative salts derived from such pharmaceutically acceptable bases include the sodium, potassium, lithium, ammonia, calcium magnesium, ferrous, ferric, zinc, manganous, aluminum, manganic, trimethylamine, triethylamine, tripropylamine, β-(dimethylamino)ethanol, triethanolamine, β-(diethylamino)ethanol, arginine, lysine, histidine, N-ethyl-piperidine, hydrabamine, choline, betaine, ethylenediamine, glucosamine, methyl glucamine, theobromine, purines, piperazine, piperidine, polyamine resins, caffeine, procaine salts. The reaction is conducted in an aqueous solution, alone or in combination with an inert, water miscible organic solvent, at a temperature of from about 0°C to about 100°C, preferably at room temperature. Typical inert, water miscible organic solvents include methanol, ethanol, isopropanol, butanol, acetone, dioxane, or tetrahydrofuran. when divalent metal salts are prepared, such as the calcium salts or magnesium salts of the acids the free acid starting material is treated with about ½ molar equivalent of pharamaceutically acceptable base. When the aluminum salts of the acids are prepared, about ⅓ molar equivalent of the pharmaceutically acceptable base are employed.

In the preferred embodiment of the present invention, the calcium salts and magnesium salts of the acids are prepared by treating the corresponding sodium or potassium salts of the acids with at least one molar equivalent of calcium chloride or magnesium chloride, respectively, in an aqueous solution, alone or in combination with an inert water miscible organic solvent, at a temperature of from about 20°C to about 100°C.

In the preferred embodiment of the present invention, the aluminum salts of the acids are prepared by treating the acids with at least ⅓ molar equivalent of an aluminum alkoxide, such as aluminum triethoxide, aluminum triprepoxide, and the like, in a hydrocarbon solvent, such as benzene, xylene, cyclohexane, and the like at a temperature of from about 20°C to about 115°C.

In the sulfo series, use of one equivalent of base provides the sulfo acid monosalts; use of two equivalents provides the disalts.

In the present specification and claims, by the term "lower alkyl" is intended a lower alkyl group containing one to five carbon atoms including straight and branched chain groups and cyclic alkyl groups, for example, methyl, ethyl, n-propyl, isopropyl, n-butyl, isobutyl, sec-butyl, t-butyl, n-pentyl, isopentyl, sec-pentyl, t-pentyl, cyclopropyl, cyclobutyl, and cyclopentyl. By the term "lower alkoxy" is intended the group "O-lower alkyl" wherein "lower alkyl" is as defined above. The term "alkyl" as used herein is intended to include the lower alkyl groups as defined above and higher straight and branched chain alkyl groups containing from six to twelve carbon atoms, for example, n-hexyl, isohexyl, n-heptyl, isoheptyl, n-octyl, isooctyl, n-nonanyl, n-decanyl, n-undecanyl, n-dodecanyl, and the like. By the term "alkoxy" is intended the group "O-alkyl" wherein "alkyl" is defined as above.

By the term "pharmaceutically acceptable, non-toxic esters, amides, and salts" is respectively intended an alkyl or glycerol ester; an unsubstituted, monoalkyl, dialkyl, dialkylaminoalkyl, alkoxyalkyl, or phenethyl substituted amide; and a salt as defined above.

The term "carboxylic acyl", as used herein, refers to those physiologically acceptable acyl groups, conventionally employed in the pharmaceutical art, preferably hydrocarbon carboxylic acyl. Included are acetate, propionate, butyrate, trimethylacetate, valerate, methylethylacetate, caproate, t-butylacetate, 3-methylpentanoate, enanthate, caprylate, triethylacetate, pelargonate, decanoate, undecanoate, benzoate, phenylacetate, diphenylacetate, cyclopentylpropionate, methoxyacetate, aminoacetate, diethylaminoacetate, trichloroacetate, β-chloropropionate, bicyclo[2.2.2]octane-1-carboxylate, adamantoate, dihydrogen phosphate, dibenzyl phosphate, sodium ethyl phosphate, sodium sulfate, sulfate, and the like.

In the lower alkyl sulfinyl series, the compounds possess a chiral center. The methods hereof generate each of the $d$ and $l$ and $dl$ forms and each is thus included within the scope hereof. If desired, the isomers can be separated by conventional means such as forming the alkaloid salts of the products and employing fractional crystallization.

The nomenclature herein is employed in accordance with *Chemical Abstracts*, 50, Subject Index (1962, January-June).

The following examples illustrate the method by which the present invention can be practiced. Where necessary, examples are repeated to provide starting material for subsequent examples.

EXAMPLE 1

A. A mixture of 4.188 g. of 1,3-dicarbomethoxy-4-bromo-benzene, 3.2 g. of o,p-di(methylthio)phenol, 1.32 g. of cuprous oxide in 20 ml. of dimethylacetamide is heated to 160°C and maintained thereat with stirring and under a nitrogen atmosphere. After monitoring via tlc indicates the reaction is substantially complete, the reaction mixture is diluted with water and extracted with diethylether:methylene chloride (3:1). The extracts are chromatographed on 150 g. of alumina and the uniform fractions combined to give 1,3-dicarbomethoxy-4-(o,p-di(methylthio)phenyloxy)-benzene.

B. 1,3-Dicarbomethoxy-4-(o,p-di(methylthio)-phenyloxy)-benzene (4g.) is combined with 150 ml. of 5% potassium hydroxide in methanol. The resultant mixture is refluxed for 1 hour after which time it is acidified, cooled, and filtered, to give 1,3-dicarboxy-4-(o,p-di(methylthio)phenyloxy)-benzene.

C. 2.5 Grams of 1,3-dicarboxy-4-(o,p-di(methylthio)-phenyloxy)-benzene in 20 ml. of concentrated sulfuric acid is stirred at 80°C for 1 hour. After this time, the reaction mixture is poured into 200 ml. of ice water and the resultant mixture is heated on a steam bath for 15 minutes. The mixture is cooled and filtered with the precipitate being washed with water and then recrystallized from acetic acid to give 5,7-di(methylthio)-xanthone-2carboxylic acid.

The foregoing procedure can be practiced using an alternative 1,3-dicarboloweralkoxy-4-halo starting compound, such as 1,3-dicarbomethoxy-4-chloro-(or iodo)-benzene, 1,3-dicarboethoxy-4-fluoro-benzene, 1,3-dicaraboethoxy-4-bromo-benzene, and the like, with similar results. Likewise, the foregoing procedure can be practiced using an alternate 2,4-dilower alkylthiophenol starting compound to prepare the corresponding 5,7-di(lower alkylthio)-xanthone-2-carboxylic acids, e.g. 5,7-di(ethylthio)-xanthone-2-carboxylic acid, 5,7-di(n-propylthio)-xanthone-2-carboxylic acid, 5,7-di(isopropylthio)-xanthone-2-carboxylic acid, 5,7-di(n-butylthio)-xanthone-2-carboxylic acid, 5,7-di(isobutylthio)-xanthone-2-carboxylic acid, 5,7-di(sec-butylthio)-xanthone-2-carboxylic acid, 5,7-di(t-butylthio)-xanthone-2-carboxylic acid, 5,7-di(n-pentylthio)-xanthone-2-carboxylic acid, and 5,7-di(cyclopentylthio)-xanthone-2carboxylic acid.

EXAMPLE 2

A mixture of four grams of 5,7-di(methylthio)-xanthone-2carboxylic acid, 10 g. of methyl iodide, and 10 g. of lithium carbonate in 50 ml. of dimethylformamide is stirred at room temperature for a period of 16 hours. After this period of time, the reaction mixture is poured into dilute hydrochloric acid-ice and the resultant mixture extracted with ethyl acetate. The extracts are filtered through alumina to give methyl 5,7-di(methylthio)-xanthone-2-carboxylate which can be recrystallized from methanol.

Similarly, the foregoing method is used to prepare the methyl esters of the other products of Example 1. By use of alternate lower alkyl iodides in the above procedure, the corresponding lower alkyl esters of these compounds are prepared.

EXAMPLE 3

Methyl 5,7-di(methylthio)-xanthone-2-carboxylate (927 mg.) in 60 ml. of methylene chloride is cooled to 0°C (ice). m-Chloroperbenzoic acid (555 mg.) is then added and the mixture is stirred at 0°C for 75 minutes. The reaction mixture is then filtered through alumina and washed with methylene chloride to give methyl 5,7-di(methylsulfinyl)-xanthone-2-carboxylate which can be recrystallized from benzene/heptane.

Methyl 5,7-di(methylsulfinyl)-xanthone-2-carboxylate (720 mg.), 75 ml. of ethanol, and 10 ml. of 5% sodium hydroxide are refluxed for 30 minutes. The mixture is cooled, partially evaporated and acidified. The precipitate is filtered off, washed and dried to give 5,7-di(methylsulfinyl)-xanthone-2-carboxylic acid which can be recrystallized from acetic acid.

Likewise from the respective starting compounds are prepared the following compounds:

5,7-di(isopropylsulfinyl)-xanthone-2-carboxylic acid,
5,7-di(ethylsulfinyl)-xanthone-2-carboxylic acid,
5,7-di(n-propylsulfinyl)-xanthone-2-carboxylic acid,
5,7-di(n-butylsulfinyl)-xanthone-2-carboxylic acid,
5,7-di(sec-butylsulfinyl)-xanthone-2-carboxylic acid,
5,7-di(isobutylsulfinyl)-xanthone-2-carboxylic acid,
5,7-di(t-butylsulfinyl)-xanthone-2-carboxylic acid,
5,7-di(n-pentylsulfinyl)-xanthone-2-carboxylic acid, and
5,7-di(cyclopentylsulfinyl)-xanthone-2-carboxylic acid.

The above procedure (paragraph one) can be practiced upon the corresponding acid starting compounds of Example 1 to give the same products, without the need of the final hydrolysis step.

EXAMPLE 4

Methyl 5,7-di(methylthio)-xanthone-2-carboxylate (764 mg.), 2 ml. of hydrogen peroxide (30%), and 40 ml. of acetic acid are heated on the steam bath (80°C) for 90 minutes. The indicates the absence of starting material. The mixture is diluted with 60 ml. of hot water, and the mixture is cooled, the solid is filtered off and dried to give methyl 5,7-di(methylsulfonyl)-xanthone-2-carboxylate which can be recrystallized from acetic acid/water.

Methyl 5,7-di(methylsulfonyl)-xanthone-2-carboxylate (660 mg.), 1 g. of potassium hydroxide, and 60 ml. of 80% aqueous ethanol are refluxed for 30 minutes. The mixture is filtered, acidified, and the solid filtered off to give 5,7-di(methylsulfonyl)-xanthone-2-carboxylic acid.

Likewise, from the respective starting compounds are prepared the following compounds:

5,7-di(isopropylsulfonyl)-xanthone-2-carboxylic acid,
5,7-di(ethylsulfonyl)-xanthone-2-carboxylic acid,
5,7-di(n-propylsulfonyl)-xanthone-2-carboxylic acid,
5,7-di(n-butylsulfonyl)-xanthone-2-carboxylic acid,
5,7-di(sec-butylsulfonyl)-xanthone-2-carboxylic acid,
5,7-di(isobutylsulfonyl)-xanthone-2-carboxylic acid,
5,7-di(t-butylsulfonyl)-xanthone-2-carboxylic acid,
5,7-di(n-pentylsulfonyl)-xanthone-2-carboxylic acid, and
5,7-di(cyclopentylsulfonyl)-xanthone-2-carboxylic acid.

The above procedure (paragraph one) can be practiced upon the corresponding acid starting compounds of Example 1 to give the same products, without the need of the final hydrolysis step.

EXAMPLE 5

The compound 5,7-dimethoxyxanthone-2-carboxylic acid is prepared from o,p-dimethoxyphenol according to the procedures A), B) and C) of Example 1.

A mixture of 11 g. of 5,7-dimethoxyxanthone-2-carboxylic acid in 100 ml. of concentrated aqueous hydrogen iodide and 100 ml. of acetic acid is refluxed for 4 hours. After this time, the mixture is cooled, diluted with water, and filtered. The precipitate is washed and dried to give 5,7-dihydroxyxanthone-2-carboxylic acid.

Alternatively, the hydroxy compound can be prepared according to the procedure of Example 1.

Methyl 5,7-dihydroxyxanthene-2-carboxylate is prepared from the acid by the procedure of Example 2.

To a solution of 6.2 g. of methyl 5,7-dihydroxyxanthone-2-carboxylate in 100 ml. of dimethylformamide are added 1 g. of sodium hydride. The mixture is stirred for 10 minutes at room temperature under nitrogen. Dimethylthiocarbamoyl chloride (3 g.) is then added thereto and the resultant mixture stirred at 70°C for 6 hours and then at room temperature for 16 hours. The mixture is then poured into 200 ml. of water containing 1 ml. of acetic acid, the resultant mixture is filtered and the solid dried to give methyl 5,7-di(dimethylthiocarbamoyloxy)-xanthone-2-carboxylate.

Methyl 5,7-di(dimethylthiocarbamoyloxy)-xanthone-2-carboxylate (8 g.) in 150 ml. of sulfolane is stirred at 230°C undner nitrogen. After a total of 6 hours under these conditions, tlc indicates the absence of starting material. The mixture is cooled to 80°C and 150 ml. of hot water are slowly added. The mixture is then cooled and the filtered solid washed with water and dried to give methyl 5,7-di(dimethylcarbamoylthio)-xanthone-2-carboxylate.

Methyl 5,7-di(dimethylcarbamoylthio)-xanthone-2-carboxylate (7.5 g.), 10 g. of potassium hydroxide and 250 ml. of 80% aqueous ethanol is refluxed for one hour. After this time, 250 ml. of water are added and the mixture is treated with charcoal, filtered, acidified. The product is filtered off and dried to give 5,7-dimercaptoxanthone-2-carboxylic acid.

EXAMPLE 6

One gram of 5,7-dimercaptoxanthone2-carboxylic acid is dissolved in 30 ml. of acetic acid containing 3 ml. of concentrated hydrochloric acid under warming. The solution is then saturated with chlorine gas and stirred at room temperature overnight. The solution is then diluted with water and the precipitate filtered off, washed, and dried to give 5,7-di-(chlorosulfonyl)-xanthone-2-carboxylic acid.

EXAMPLE 7

The thus prepared chlorosulfonyl compound is then treated with aqueous potassium hydroxide, as described in Example 5, last paragraph, to give 5,7-disulfoxanthone-2-carboxylic acid.

EXAMPLE 8

A mixture of 1 g. of 5,7-chlorosulfonylxanthone-2-carboxylic acid, 2 ml. of concentrated aqueous ammonia, and 20 ml. of dioxane is stirred at room temperature overnight. The mixture is then diluted with watter, acidified, and the solid filtered off and dried to give 5,7-di(sulfamoyl)-xanthone-2-carboxylic acid.

Upon substituting a primary amine, such as methylamine and ethylamine, or a secondary amine, such as dimethylamine and diethylamine, for ammonia in the above method, the corresponding C-5,7-di(N-monolower alkylsulfamoyl) and di(N,N-dilower alkylsulfamoyl) products are obtained, e.g.:

5,7-di(methylsulfamoyl)-xanthone-2-carboxylic acid,
5,7-di(ethylsulfamoyl)-xanthone-2-carboxylic acid,
5,7-di(n-propylsulfamoyl)-xanthone-2-carboxylic acid,
5,7-di(isopropylsulfamoyl)-xanthone-2-carboxylic acid,
5,7-di(dimethylsulfamoyl)-xanthone-2-carboxylic acid,
5,7-di(diethylsulfamoyl)-xanthone-2-carboxylic acid,
5,7-di(di-n-propylsulfamoyl)-xanthone-2-carboxylic acid,
5,7-di(di-isopropylsulfamoyl)-xanthone-2-carboxylic acid, and so froth.

EXAMPLE 9

The compounds 5,7-di(lower alkyl)-xanthone-2-carboxylic acid, e.g.:

5,7-diethylxanthone-2-carboxylic acid,
5,7-di-n-propylxanthone-2-carboxylic acid,
5,7-di-n-butylxanthone-2-carboxylic acid,
5,7-di-sec-butylxanthone-2-carboxylic acid,
5,7-di-n-pentylxanthone-2-carboxylic acid,
5,7-di-isopentylxanthone-2-carboxylic acid, and so forth are prepared from o,p-diloweralkylphenols according to the procedures A), B) and C) of Example 1.

A suspension of 2.5 g. of 5,7-diethylxanthone-2-carboxylic acid and 5 g. of chromic oxide in 190 ml. of acetic acid and 10 ml. of acetic anhydride is stirred at room temperature for a period of 6 hours. After monitoring the reaction by tlc indicates the absence of starting material, 10 ml. of isopropanol are added and the resultant mixture warmed on the steam bath. Water (200 ml.) is then added portionwise and the resultant mixture is cooled to room temperature. The precipitate is filtered off, washed, and dried to obtain 5,7-diacetylxanthone-2-carboxylic acid.

Similarly, the other 5,7-dialkanoylxanthone-2-carboxylic acid compounds are prepared, e.g.:

5,7-dipropionylxanthone-2-carboxylic acid,
5,7-di(n-butyryl)-xanthone-2-carboxylic acid,
5,7-di(sec-butyryl)xanthone-2-carboxylic acid,
5,7-dipentanoylxanthone-2-carboxylic acid,
5,7-di(isopentanoyl)-xanthone-2-carboxylic acid, and so forth.

EXAMPLE 10

To a solution of three grams of 5,7-diacetylxanthone-2-carboxylic acid in 90 ml. of methanol are added 3 g. of sodium borohydride in 30 ml. of water at a temperature of from 25° to 30°C, with stirring over a period of about 30 minutes. After 15 minutes, under these conditions, 50 ml. of water and 5 ml. of acetic acid are added and the resultant mixture is stripped of solvent. The resultant mixture is extracted with methylene chloride and washed with bicarbonate and water. The washed extracts are concentrated to give 5,7-di-(1-hydroxyethyl)-xanthone-2-carboxylic acid.

Similarly, the other 5,7-(1-hydroxyalkyl)-xanthone-2-carboxylic acid compounds are prepared, e.g.:

5,7-(1-hydroxy-n-proypl)-xanthone-2-carboxylic acid,
5,7-(1-hydroxy-n-butyl)-xanthone-2-carboxylic acid,
5,7-(1-hydroxy-sec-butyl)-xanthone-2-carboxylic acid,
5,7-(1-hydroxy-n-pentyl)-xanthone-2-carboxylic acid,
5,7-(1-hydroxy-isopentyl)-xanthone-2-carboxylic acid, and so forth.

EXAMPLE 11

The compounds 5-alkyl or -alkoxy-7-(lower-alkythio)-xanthone-2-carboxylic acid, e.g.:

5-methyl-7-(methylthio)-xanthone-2-carboxylic acid,
5-ethyl-7-(methylthio)-xanthone-2-carboxylic acid,
5-n-propyl-7-(methylthio)-xanthone-2-carboxylic acid,
5-isopropyl-7-(methylthio)-xanthone-2-carboxylic acid,
5-n-butyl-7-(methylthio)-xanthone-2-carboxylic acid,
5-isobutyl-7-(methylthio)-xanthone-2-carboxylic acid,
5-sec-butyl-7-(methylthio)-xanthone-2-carboxylic acid,
5-t-butyl-7-(methylthio)-xanthone-2-carboxylic acid,
5-n-pentyl-7-(methylthio)-xanthone-2-carboxylic acid,
5-isopentyl-7-(methylthio)-xanthone-2-carboxylic acid,
5-n-hexyl-7-(methylthio)-xanthone-2-carboxylic acid,
5-n-octyl-7-(methylthio)-xanthone-2-carboxylic acid,
5-n-dodecyl-7-(methylthio)-xanthone-2-carboxylic acid,
5-cyclopentyl-7-(methylthio)-xanthone-2-carboxylic acid,
5-methoxy-7-(methylthio)-xanthone-2-carboxylic acid,
5-ethoxy-7-(methylthio)-xanthone-2-carboxylic acid,
5-n-proxy-7-(methylthio)-xanthone-2-carboxylic acid,
5-isopropxy-7-(methylthio)-xanthone-2-carboxylic acid,
5-n-butoxy-7-(methylthio)-xanthone-2-carboxylic acid,
5-isobutoxy-7-(methylthio)-xanthone-2-carboxylic acid,
5-sec-butoxy-7-(methylthio)-xanthone-2-carboxylic acid,
5-t-butoxy-7-(methylthio)-xanthone-2-carboxylic acid,
5-n-pentyloxy-7-(methylthio)-xantone-2-carboxylic acid,
5-isopentyloxy-7-(methylthio)-xanthone-2-carboxylic acid,
5-n-hexyloxy-7-(methylthio)-xanthone-2-carboxylic acid,
5-n-octyloxy-7-(methylthio)-xanthone-2-carboxylic acid,
5-n-dodecyloxy-7-(methylthio)-xanthone-2-carboxylic acid, 5-cyclopentyloxy-7-(methylthio)-xanthone-2-carboxylic acid, and the corresponding 5-substituted 28 compounds in each of the 7-ethylthio-, 7-n-propylthio-, 7-isopropylthio-, 7-n-butylthio-, 7-isobutylthio-, 7-sec-butylthio-, 7-t-butylthio-, 7-n-pentylthio 7-isopentylthio-, and 7-(cyclopentylthio)-xanthone-2-carboxylic acid series are prepared according to the procedures (A), (B) and (C) of Example 1.

The thus prepared compounds are treated in accordance with the procedures of Examples 3 and 4 to prepare the corresponding 5-substituted-7-loweralkylsulfinyl- and -7-loweralkylsulfonylxanthone-2-carboxylic acid compounds, to wit:

5-methyl-7-methylsulfinylxanthone-2-carboxylic acid,
5-methyl-7-methylsulfonylxanthone-2-carboxylic acid,
5-ethyl-7-methylsulfinylxanthone-2-carboxylic acid,
5-ethyl-7-methylsulfonylxanthone-2-carboxylic acid,
5-n-propyl-7-methylsulfinylxanthone-2-carboxylic acid,
5-n-propyl-7-methylsulfonylxanthone-2-carboxylic acid,
5-isopropyl-7-methylsulfinylxanthone-2-carboxylic acid,
5-isopropyl-7-methylsulfonylxanthone-2-carboxylic acid,
5-n-octyl-7-methylsulfinylxanthone-2-carboxylic acid,
5-n-octyl-7-methylsulfonylxanthone-2-carboxylic acid,
and so forth,
5-methoxy-7-methylsulfinylxanthone-2-carboxylic acid,
5-methoxy-7-methylsulfonylxanthone-2-carboxylic acid,
5-ethoxy-7-methylsulfinylxanthone-2-carboxylic acid,
5-ethoxy-7-methylsulfonylxanthone-2-carboxylic acid,
5-n-propoxy-7-methylsulfinylxanthone-2-carboxylic acid,
5-n-propoxy-7-methylsulfonylxanthone-2-carboxylic acid,
5-isopropoxy-7-methylsulfinylxanthone-2-carboxylic acid,
5-isopropoxy-7-methylsulfonylxanthone-2-carboxylic acid,
5-n-octyloxy-7-methylsulfinylxanthone-2-carboxylic acid,
5-n-octyloxy-7-methylsulfonylxanthone-2-carboxylic acid,
and so forth,
5-methyl-7-ethylsulfinylxanthone-2-carboxylic acid,
5-methyl-7-ethylsulfonylxanthone-2-carboxylic acid,
5-ethyl-7-ethylsulfinylxanthone-2-carboxylic acid,
5-ethyl-7-ethylsulfonylxanthone-2-carboxylic acid,
5-n-propyl-7-ethylsulfinylxanthone-2-carboxylic acid,
5-n-propyl-7-ethylsulfonylxanthone-2-carboxylic acid,
5-isopropyl-7-ethylsulfinylxanthone-2-carboxylic acid,
5-isopropyl-7-ethylsulfonylxanthone-2-carboxylic acid,
5-n-octyl-7-ethylsulfinylxanthone-2-carboxylic acid,
5-n-octyl-7-ethylsulfonylxanthone-2-carboxylic acid,
and so forth,
5-methoxy-7-ethylsulfinylxanthone-2-carboxylic acid,
5-methoxy-7-ethylsulfonylxanthone-2-carboxylic acid,
5-ethoxy-7-ethylsulfinylxanthone-2-carboxylic acid,
5-ethoxy-7-ethylsulfonylxanthone-2-carboxylic acid,
5-n-propoxy-7-ethylsulfinylxanthone-2-carboxylic acid,
5-n-propoxy-7-ethylsulfonylxanthone-2-carboxylic acid,
5-isopropoxy-7-ethylsulfinylxanthone-2-carboxylic acid,
5-isopropoxy-7-ethylsulfonylxanthone-2-carboxylic acid,
5-n-octyloxy-7-ethylsulfinylxanthone-2-carboxylic acid,
5-n-octyloxy-7-ethylsulfonylxanthone-2-carboxylic acid,
and so forth,
5-methyl-7-n-propylsulfinylxanthone-2-carboxylic acid,
5-methyl-7-n-propylsulfonylxanthone-2-carboxylic acid,
5-ethyl-7-n-propylsulfinylxanthone-2-carboxylic acid,
5-ethyl-7-propylsulfonylxanthone-2-carboxylic acid,
5-n-propyl-7-n-propylsulfinylxanthone-2-carboxylic acid,
5-n-propyl-7-n-propylsulfonylxanthone-2-carboxylic acid,
5-isopropyl-7-n-propylsulfinylxanthone-2-carboxylic acid,
5-isopropyl-7-n-propylsulfonylxanthone-2-carboxylic acid
5-n-octyl-7-n-propylsulfinylxanthone-2-carboxylic acid,
5-n-octyl-7-n-propylsulfonylxanthone-2-carboxylic acid,
and so forth,
5-methoxy-7-n-propylsulfinylxanthone-2-carboxylic acid,
5-methoxy-7-n-propylsulfonylxanthone-2-carboxylic acid,
5-ethoxy-7-n-propylsulfinylxanthone-2-carboxylic acid,
5-ethoxy-7-n-propylsulfonylxanthone-2-carboxylic acid,
5-n-propoxy-7-n-propylsulfinylxanthone-2-carboxylic acid,
5-n-propoxy-7-n-propylsulfonylxanthone-2-carboxylic acid,
5-isopropoxy-7-n-propylsulfinylxanthone-2-carboxylic acid,
5-isopropoxy-7-n-propylsulfonylxanthone-2-carboxylic acid,
5-n-octyloxy-7-n-propylsulfinylxanthone-2-carboxylic acid,
5-n-octyloxy-7-n-propylsulfonylxanthone-2-carboxylic acid,
and so forth,
5-methyl-7-isopropylsulfinylxanthone-2-carboxylic acid,
5-methyl-7-isopropylsulfonylxanthone-2-carboxylic acid,
5-ethyl-7-isopropylsulfinylxanthone-2-carboxylic acid,
5-ethyl-7-isopropylsulfonylxanthone-2-carboxylic acid, 5-n-propyl-7-isopropylsulfinylxanthone-2-carboxylic acid,
5-n-propyl-7-isopropylsulfonylxanthone-2-carboxylic acid,
5-isopropyl-7-isopropylsulfinylxanthone-2-carboxylic acid,
5-isopropyl-7-isopropylsulfonylxanthone-2-carboxylic acid,
5-n-octyl-7-isopropylsulfinylxanthone-2-carboxylic acid,
5-n-octyl-7-isopropylsulfonylxanthone-2-carboxylic acid,
and so forth,
5-methoxy-7-isopropylsulfinylxanthone-2-carboxylic acid,
5-methoxy-7-isopropylsulfonylxanthone-2-carboxylic acid,
5-ethoxy-7-isopropylsulfinylxanthone-2-carboxylic acid,
5-ethoxy-7-isopropylsulfonylxanthone-2-carboxylic acid,
5-n-propoxy-7-isopropylsulfinylxanthone-2-carboxylic acid,
5-n-propoxy-7-isopropylsulfonylxanthone-2-carboxylic acid,
5-isopropoxy-7-isopropylsulfinylxanthone-2-carboxylic acid,
5-isopropoxy-7-isopropylsulfonylxanthone-2-carboxylic acid,
5-n-octyloxy-7-isopropylsulfinylxanthone-2-carboxylic acid,
5-n-octyloxy-7-isopropylsulfonylxanthone-2-carboxylic acid,
and so forth.

In a similar manner, the following compounds are also prepared:
5-n-butoxy-7-methylsulfonylxanthone-2-carboxylic acid,
5-cyclopentyloxy-7-methylsulfinylxanthone-2-carboxylic acid,
5-n-pentyloxy-7-methylsulfinylxanthone-2-carboxylic acid, and
5-isopentyloxy-methylsulfinylxanthone-2-carboxylic acid.

EXAMPLE 12

Example 11 is repeated to prepare the 5-(lower alkylthio)-7-alkyl or -alkoxy-xanthone-2-carboxylic acid compounds and the sulfinyl and sulfonyl compounds otherwise corresponding thereto, i.e.:
5-methylthio-7-methylxanthone-2-carboxylic acid,
5-methylthio-7-ethylxanthone-2-carboxylic acid,
5-methylthio-7-n-propylxanthone-2-carboxylic acid,
5-methylthio-7-isopropylxanthone-2-carboxylic acid,
5-methylthio-7-n-octylxanthone-2-carboxylic acid,
and so forth,
5-methylthio-7-methoxyxanthone-2-carboxylic acid,
5-methylthio-7-ethoxyxanthone-2-carboxylic acid,
5-methylthio-7-n-propoxyxanthone-2-carboxylic acid,
5-methylthio-7-isopropoxyxanthone-2-carboxylic acid,
5-methylthio-7-n-octyloxyxanthone-2-carboxylic acid, and so forth, and the corresponding total of 28 compounds in each of the 5-ethylthio-, 5-n-propyl-, 5-n-propylthio-, 5-isopropylthio, and so forth series.
5-methylsulfinyl-7-methylxanthone-2-carboxylic acid,
5-methylsulfonyl-7-methylxanthone-2-carboxylic acid,
5-methylsulfinyl-7-ethylxanthone-2-carboxylic acid,
5-methylsulfonyl-7-ethylxanthone-2-carboxylic acid,
5-methylsulfinyl-7-n-propylxanthone-2-carboxylic acid,
5-methylsulfonyl-7-n-propylxanthone-2-carboxylic acid,
5-methylsulfinyl-7-isopropylxanthone-2-carboxylic acid,
5-methylsulfonyl-7-isopropylxanthone-2-carboxylic acid, 5-methylsulfinyl-7-n-octylxanthone-2-carboxylic acid,
5-methylsulfonyl-7-n-octylxanthone-2-carboxylic acid, 5-methylsulfinyl-7-methoxyxanthone-2-carboxylic acid, 5-methylsulfonyl-7-methoxyxanthone-2-carboxylic acid,
5-methylsulfinyl-7-ethoxyxanthone-2-carboxylic acid,
5-methylsulfonyl-7-ethoxyxanthone-2-carboxylic acid,
5-methylsulfinyl-7-n-propoxyxanthone-2-carboxylic acid, 5-methylsulfonyl-7-n-propoxyxanthone-2-carboxylic acid,
5-methylsulfinyl-7-isopropoxyxanthone-2-carboxylic acid,
5-methylsulfonyl-7-isopropoxyxanthone-2-carboxylic acid,
5-methylsulfinyl-7-octyloxyxanthone-2-carboxylic acid,
5-methylsulfonyl-7-octyloxyxanthone-2-carboxylic acid
and so forth,
5-ethylsulfinyl-7-methylxanthone-2-carboxylic acid,
5-ethylsulfonyl-7-methylxanthone-2-carboxylic acid,
5-ethylsulfinyl-7-ethylxanthone-2-carboxylic acid,
5-ethylsulfonyl-7-ethylxanthone-2-carboxylic acid,
5-ethylsulfinyl-7-n-propylxanthone-2-carboxylic acid,
5-ethylsulfonyl-7-n-propylxanthone-2-carboxylic acid,
5-ethylsulfinyl-7-isopropylxanthone-2-carboxylic acid,
5-ethylsulfonyl-7-isopropylxanthone-2-carboxylic acid,
5-ethylsulfinyl-7-n-octylxanthone-2-carboxylic acid,
5-ethylsulfonyl-7-n-octylxanthone-2-carboxylic acid,
and so forth,
5-ethylsulfinyl-7-methoxyxanthone-2-carboxylic acid,
5-ethylsulfonyl-7-methoxyxanthone-2-carboxylic acid,
5-ethylsulfinyl-7-ethoxyxanthone-2-carboxylic acid,
5-ethylsulfonyl-7-ethoxyxanthone-2-carboxylic acid,
5-ethylsulfinyl-7-n-propoxyxanthone-2-carboxylic acid,
5-ethylsulfonyl-7-n-propoxyxanthone-2-carboxylic acid,
5-ethylsulfinyl-7-isopropoxyxanthone-2-carboxylic acid,
5-ethylsulfonyl-7-isopropoxyxanthone-2-carboxylic acid,
5-ethylsulfinyl-7-n-octyloxyxanthone-2-carboxylic acid,
5-ethylsulfonyl-7-n-octyloxyxanthone-2-carboxylic acid,
and so forth, 5-n-propylsulfinyl-7-methylxanthone-2-carboxylic acid,
5-n-propylsulfonyl-7-methylxanthone-2-carboxylic acid,
5-n-propylsulfinyl-7-ethylxanthone-2-carboxylic acid,
5-n-propylsulfonyl-7-ethylxanthone-2-carboxylic acid,
5-n-propylsulfinyl-7-n-propylxanthone-2-carboxylic acid,
5-n-propylsulfonyl-7-n-propylxanthone-2-carboxylic acid,
5-n-propylsulfinyl-7-isopropylxanthone-2-carboxylic acid,
5-n-propylsulfonyl-7-isopropylxanthone-2-carboxylic acid,
5-n-propylsulfinyl-7-n-octylxanthone-2-carboxylic acid,
5-n-propylsulfonyl-7-n-octylxanthone-2-carboxylic acid,
and so forth,
5-n-propylsulfinyl-7-methoxyxanthone-2-carboxylic acid,
5-n-propylsulfonyl-7-methoxyxanthone-2-carboxylic acid, 5-n-propylsulfinyl-17-ethoxyxanthone-2-carboxylic acid,
5-n-propylsulfonyl-7-ethoxyxanthone-2-carboxylic acid,
5-n-propylsulfinyl-7-n-propoxyxanthone-2-carboxylic acid,
5-n-propylsulfonyl-7-n-propoxyxanthone-2-carboxylic acid,
5-n-propylsulfinyl-7-isopropoxyxanthone-2-carboxylic acid, 5-n-propylsulfonyl-7-isopropoxyxanthone-2-carboxylic acid,
5-n-propylsulfinyl-7-n-octyloxyxanthone-2-carboxylic acid,
5-n-propylsulfonyl-7-n-octyloxyxanthone-2-carboxylic acid,
and so forth,
5-isopropylsulfinyl-7-methylxanthone-2-carboxylic acid,
5-isopropylsulfonyl-7-methylxanthone-2-carboxylic acid,
5-isopropylsulfinyl-7-ethylxanthone-2-carboxylic acid,
5-isopropylsulfonyl-7-ethylxanthone-2-carboxylic acid,
5-isopropylsulfinyl-7-n-propylxanthone-2-carboxylic acid,
5-isopropylsulfonyl-7-n-propylxanthone-2-carboxylic acid,
5-isopropylsulfinyl-7-isopropylxanthone-2-carboxylic acid,
5-isopropylsulfonyl-7-isopropylxanthone-2-carboxylic acid,
5-isopropylsulfinyl-7-n-octylxanthone-2-carboxylic acid,
5-isopropylsulfonyl-7-n-octylxanthone-2-carboxylic acid,
and so forth,
5-isopropylsulfinyl-7-methoxyxanthone-2-carboxylic acid,
5-isopropylsulfonyl-7-methoxyxanthone-2-carboxylic acid,
5-isopropylsulfinyl-7-ethoxyxanthone-2-carboxylic acid,
5-isopropylsulfonyl-7-ethoxyxanthone-2-carboxylic acid,
5-isopropylsulfinyl-7-n-propxyxanthone-2-carboxylic acid,
5-isopropylsulfonyl-7-n-propoxyxanthone-2-carboxylic acid,
5-isopropylsulfinyl-7-isopropoxyxanthone-2-carboxylic acid,
5-isopropylsulfonyl-7-isopropoxyxanthone-2-carboxylic acid,
5-isopropylsulfinyl-7-n-octyloxyxanthone-2-carboxylic acid,
5-isopropysulfonyl-7-n-octyloxyxanthone-2-carboxylic acid,
and so forth.

EXAMPLE 13

The compounds 5-alkyl-or -alkoxyxanthone-2-carboxylic acid are prepared according to the procedures (A), (B) and (C) of Example 1.

5-Methylxanthone-2-carboxylic acid (2.5 g.) is dissolved in 15 ml. of chlorosulfonic acid. After heating the mixture to 140°C for 3 hours, it is cooled (ice) and poured slowly into 50 ml. of 30% aqueous acetic acid. After cooling, the precipitate is filtered off, washed neutral and dried to give 5-methyl-7-chlorosulfonylxanthone-2-carboxylic acid.

In like manner, the following are prepared:
5-ethyl-7-chlorosulfonylxanthone-2-carboxylic acid,
5-n-propyl-7-chlorosulfonylxanthone-2-carboxylic acid,
5-isopropyl-7-chlorosulfonylxanthone-2-carboxylic acid,
5-n-octyl-7-chlorosulfonylxanthone-2-carboxylic acid,
5-methoxy-7-chlorosulfonylxanthone-2-carboxylic acid,
5-ethoxy-7-chlorosulfonylxanthone-2-carboxylic acid,
5-n-propoxy-7-chlorosulfonylxanthone-2carboxylic acid,
5-isopropoxy-7-chlorosulfonylxanthone-2-carboxylic acid,
5-n-octyloxy-7-chlorosulfonylxanthone-2carboxylic acid,
and so forth.

The thus prepared compounds are treated in accordance with the procedures of Example 7 to give the corresponding sulfo compounds, e.g.:
5-methyl-7-sulfoxanthone-2carboxylic acid,
5-ethyl-7-sulfoxanthone-2-carboxylic acid,
5-n-propyl-7-sulfoxanthone-2-carboxylic acid,
5-isopropyl-7-sulfoxanthone-2-carboxylic acid,
5-n-octyl-7-sulfoxanthone-2-carboxylic acid,
5-methoxy-7-sulfoxanthone-2-carboxylic acid,
5-ethoxy-7-sulfoxanthone-2-carboxylic acid,
5-n-propoxy-7-sulfoxanthone-2carboxylic acid,
5-isopropoxy-7-sulfoxanthone-2-carboxylic acid, and
5-n-octyloxy-7-sulfoxanthone-2-carboxylic acid,
or in accordance with the procedures of Example 8 to give the corresponding sulfamoyl compounds, e.g.:
5-methyl-7-sulfamoylxanthone-2-carboxylic acid,
5-ethyl-7sulfamoylxanthone-2-carboxylic acid,
5-n-propyl-7-sulfamoylxanthone-2carboxylic acid,
5-isopropyl-7-sulfamoylxanthone-2-carboxylic acid,
5-n-octyl-7-sulfamoylxanthone-2-carboxylic acid,
5-methoxy-7-sulfamoylxanthone-2-carboxylic acid,
5-ethoxy-7-sulfamoylxanthone-2-carboxylic acid, 5-n-propoxy-7-sulfamoylxanthone-2carboxylic acid,
5-isopropoxy-7-sulfamoylxanthone-2-carboxylic acid,
5-n-octyloxy-7sulfamoylxanthone-2-carboxylic acid,
5-methyl-7-methylsulfamoylxanthone-2-carboxylic acid,
5-ethyl-7-methylsulfamoylxanthone-2-carboxylic acid,
5-n-propyl-7-methylsulfamoylxanthone-2-carboxylic acid,
5-isopropyl-7-methylsulfamoylxanthone-2-carboxylic acid,
5-n-octyl-7-methylsulfamoylxanthone-2-carboxylic acid,
5-methoxy-7-methylsulfamoylxanthone-2-carboxylic acid,
5-ethoxy-7-methylsulfamoylxanthone-2-carboxylic acid,
5-n-propoxy-7-methylsulfamoylxanthone-2-carboxylic acid,
5-isopropoxy-7-methylsulfamoylxanthone-2-carboxylic acid,
5-n-octyloxy-7-methylsulfamoylxanthone-2-carboxylic acid,
and so forth,
5-methyl-7-dimethylsulfamoylxanthone-2-carboxylic acid,
5-ethyl-7-dimethylsulfamoylxanthone-2-carboxylic acid,
5-n-propyl-7-dimethylsulfamoylxanthone-2-carboxylic acid,
5-isopropyl-7-dimethylsulfamoylxanthone-2-carboxylic acid,
5-n-octyl-7-dimethylsulfamoylxanthone-2-carboxylic acid,
5-methoxy-7-dimethylsulfamoylxanthone-2-carboxylic acid,
5-ethoxy-7-dimethylsulfamoylxanthone-2-carboxylic acid,
5-n-propoxy-7-dimethylsulfamoylxanthone-2-carboxylic acid,
5-isopropoxy-7-dimethylsulfamoylxanthone-2-carboxylic acid,
5-n-octyloxy-7-dimethylsulfamoylxanthone-2-carboxylic acid,
and so forth.

EXAMPLE 14

The procedure of Example 13 is repeated to prepare the corresponding 5-chlorosulfonyl-, 5-sulfo- and 5-sulfamoyl- compounds in the 7-lower alkyl- or -lower alkoxy series, e.g.:
5-chlorosulfonyl-7-methylxanthone-2-carboxylic acid,
5-chlorosulfonyl-7-ethylxanthone-2-carboxylic acid,
5-chlorosulfonyl-7-n-propylxanthone-2-carboxylic acid,
5-chlorosulfonyl-7-isopropylxanthone-2-carboxylic acid,
5-chlorosulfonyl-7-n-octylxanthone-2-carboxylic acid,
5-chlorosulfonyl-7-methoxyxanthone-2-carboxylic acid,
5-chlorosulfonyl-7-ethoxyxanthone-2-carboxylic acid,
5-chlorosulfonyl-7-n-propoxyxanthone-2-carboxylic acid,
5-chlorosulfonyl-7-isopropoxyxanthone-2-carboxylic acid,
5-chlorosulfonyl-7-n-octyloxyxanthone-2-carboxylic acid,
5-sulfo-7-methylxanthone-2-carboxylic acid,
5-sulfo-7-ethylxanthone-2-carboxylic acid,
5-sulfo-7-n-propylxanthone-2-carboxylic acid,
5-sulfo-7-isopropylxanthone-2-carboxylic acid,
5-sulfo-7-n-octylxanthone-2-carboxylic acid,
5-sulfo-7-methoxyxanthone-2-carboxylic acid,
5-sulfo-7-ethoxyxanthone-2-carboxylic acid,
5-sulfo-7-n-propoxyxanthone-2-carboxylic acid,
5-sulfo-7-isopropoxyxanthone-2-carboxylic acid,
5-sulfo-7-n-octyloxyxanthone-2-carboxylic acid,
5-sulfamoyl-7-methylxanthone-2-carboxylic acid,
5-sulfamoyl-7-ethylxanthone-2-carboxylic acid,
5-sulfamoyl-7-n-propylxanthone-2-carboxylic acid,
5-sulfamoyl-7-isopropylxanthone-2-carboxylic acid,
5-sulfamoyl-7-n-octylxanthone-2-carboxylic acid,
5-sulfamoyl-7-methoxyxanthone-2-carboxylic acid,
5-sulfamoyl-7-ethoxyxanthone-2-carboxylic acid,
5-sulfamoyl-7-n-propoxyxanthone-2-carboxylic acid,
5-sulfamoyl-7-isopropoxyxanthone-2-carboxylic acid,
5-sulfamoyl-7-n-octyloxyxanthone-2-carboxylic acid,
5-methylsulfamoyl-7-methylxanthone-2-carboxylic acid,
5-methylsulfamoyl-7-ethylxanthone-2-carboxylic acid,
5-methylsulfamoyl-7-n-propylxanthone-2-carboxylic acid,
5-methylsulfamoyl-7-isopropylxanthone-2-carboxylic acid,
5-methylsulfamoyl-7-n-octylxanthone-2-carboxylic acid,
5-methylsulfamoyl-7-methoxyxanthone-2-carboxylic acid,
5-methylsulfamoyl-7-ethoxyxanthone-2-carboxylic acid,
5-methylsulfamoyl-7-n-propoxyxanthone-2-carboxylic acid,
5-methylsulfamoyl-7-isopropoxyxanthone-2-carboxylic acid,
5-methylsulfamoyl-7-n-octyloxyxanthone-2-carboxylic acid,
5-dimethylsulfamoyl-7-methylxanthone-2-carboxylic acid,
5-dimethylsulfamoyl-7-ethylxanthone-2-carboxylic acid,
5-dimethylsulfamoyl-7-n-propylxanthone-2-carboxylic acid,
5-dimethylsulfamoyl-7-isopropylxanthone-2-carboxylic acid,
5-dimethylsulfamoyl-7-n-octylxanthone-2-carboxylic acid,
5-dimethylsulfamoyl-7-methoxyxanthone-2-carboxylic acid,
5-dimethylsulfamoyl-7-ethoxyxanthone-2-carboxylic acid,
5-dimethylsulfamoyl-7-n-propoxyxanthone-2-carboxylic acid,
5-dimethylsulfamoyl-7-isopropoxyxanthone-2-carboxylic acid.
5-dimethylsulfamoyl-7-isopropoxyxanthone-2-carboxylic acid,
5-dimethylsulfamoyl-7-n-octyloxyxanthone-2-carboxylic acid,
and so forth.

EXAMPLE 15

To a solution of 25 g. of 7-methylxanthone-2-carboxylic acid in 200 ml. of triethylene glycol are added 18 g. of potassium hydroxide in 12.1 g. of 95% hydrazine. The resultant mixture is heated to reflux (155°C) and maintained thereat for 1 hour. The distillate is removed and the temperature is held at a temperature of about 200°C for 2 hours. The mixture is then cooled to 68°C and 200 ml. of water is added and the resultant solution poured into 110 ml. of water containing 60 ml. of concentrated hydrochloric acid. The resultant mixture is heated to 90°C, cooled to room temperature and filtered to give 7-methylxanthene-2-carboxylic acid.

Twenty-six grams of 7-methylxanthene-2-carboxylic acid is added to 400 ml. of absolute methanol. To the resultant solution are added 18 ml. of concentrated sulfuric acid and the mixture is then heated at reflux for about 2 hours. The mixture is then cooled to 40°C and sufficient water is added to bring the total volume to 1400 ml. The resultant mixture is then filtered to give methyl 7-methylxanthene-2-carboxylate.

A mixture of 130 g. of methyl 7-methylxanthene-2-carboxylate in 200 ml. of dichloroethane is cooled to −5°C and to the cooled solution are added 4.95 ml. of acetyl chloride and then 17.0 g. of aluminum trichloride. The resultant solution is stirred at room temperature for 1.75 hours. After this time, the solution is poured into a mixture of 300 g. of ice, 700 ml. of water and 200 ml. of concentrated hydrochloric acid. The mixture is then extracted with three 500 ml. portions of methylene chloride. The combined extracts are washed with 10% aqueous potassium hydroxide solution and the washed solution evaporated to give methyl 5-acetyl-7-methylxanthene-2-carboxylate.

To a solution of 1.42 g. of methyl 5-acetyl-7-methylxanthene-2-carboxylate in 120 ml. of acetone and 15 ml. of dimethylformamide are added 3.0 g. of magnesium sulfate and 2.5 ml. of 8 N chromic acid in 8 N sulfuric acid. The resultant mixture is stirred at room temperature for 50 minutes after which time a solution of 4 g. of sodium bisulfite in 20 ml. of water are added. After this time, 250 ml. of water and 25 ml. of sulfuric acid:water (1:1) are added. The mixture is stripped of solvent and filtered. The precipitate is washed with 50 ml. of water to give methyl 5-acetyl-7-methylxanthone-2-carboxylate which is recrystallized from methanol (displacement from methylene chloride solution).

A solution of 2 g. of methyl 5-acetyl-7-methylxanthone-2-carboxylate in 200 ml. of 10% aqueous, 10% potassium hydroxide in methanol is heated at reflux under a nitrogen atmosphere for 45 minutes. After this time, 20 ml. of water are added and the resultant mixture heated at reflux for 35 minutes. Water (300 ml.) is then added and the resultant mixture acidified and filtered to give 5-acetyl-7-methylxanthone-2-carboxylic acid.

Upon using the appropriate acyl chloride reagent in the foregoing procedure the other 5-acyl-7-methylxanthone-2-carboxylic acids, see Example 9, can be prepared and the 5-acyl-7-alkyl- or -alkoxy compounds are also thus prepared, e.g.:

5-propionyl-7-methylxanthone-2-carboxylic acid,
5-acetyl-7-ethylxanthone-2-carboxylic acid,
5-propionyl-7-ethylxanthone-2-carboxylic acid,
5-acetyl-7-n-propylxanthone-2-carboxylic acid,
5-propionyl-7-n-propylxanthone-2-carboxylic acid,
5-acetyl-7-isopropylxanthone-2-carboxylic acid,
5-propionyl-7-isopropylxanthone-2-carboxylic acid,
5-acetyl-7-n-octylxanthone-2-carboxylic acid,
5-propionyl-7-n-octylxanthone-2-carboxylic acid,
5-acetyl-7-methoxyxanthone-2-carboxylic acid,
5-propionyl-7-methoxyxanthone-2-carboxylic acid,
5-acetyl-7-ethoxyxanthone-2-carboxylic acid,
5-propionyl-7-ethoxyxanthone-2-carboxylic acid,
5-acetyl-7-n-propoxyxanthene-2-carboxylic acid, 5-propionyl-7-n-propoxyxanthone-2-carboxylic acid,
5-acetyl-7-isopropoxyxanthone-2-carboxylic acid,
5-propionyl-7-isopropoxyxanthone-2-carboxylic acid,
5-acetyl-7-n-octyloxyxanthone-2-carboxylic acid,
5-propionyl-7-n-octyloxyxanthone-2-carboxylic acid, and the 5-butyryl and 5-cyclopropylcarbonyl compounds corresponding thereto, and so forth.

EXAMPLE 16

The procedure of Example 15 is repeated with alternate starting compounds to prepare the following:
5-methyl-7-acetylxanthone-2-carboxylic acid,
5-methyl-7-propionylxanthone-2-carboxylic acid,
5-ethyl-7-acetylxanthone-2-carboxylic acid,
5-ethyl-7-propionylxanthone-2-carboxylic acid,
5-n-propyl-7-acetylxanthone-2-carboxylic acid,
5-n-propyl-7-propionylxanthone-2-carboxylic acid,
5-isopropyl-7-acetylxanthone-2-carboxylic acid,
5-isopropyl-7-propionylxanthone-2-carboxylic acid,
5-n-octyl-7-acetylxanthone-2-carboxylic acid,
5-n-octyl-7-propionylxanthone-2-carboxylic acid,
5-methoxy-7-acetylxanthone-2-carboxylic acid,
5-methoxy-7-propionylxanthone-2-carboxylic acid,
5-ethoxy-7-acetylxanthone-2-carboxylic acid,
5-ethoxy-7-propionylxanthone-2-carboxylic acid,
5-n-propoxy-7-acetylxanthone-2-carboxylic acid,
5-n-propoxy-7-propionylxanthone-2-carboxylic acid,
5-isopropoxy-7-acetylxanthone-2-carboxylic acid,
5-isopropoxy-7-propionylxanthone-2-carboxylic acid,
5-n-octyloxy-7-acetylxanthone-2-carboxylic acid,
5-n-octyloxy-7-propionylxanthone-2-carboxylic acid, and the 7-butyryl and 7-cyclopropylcarbonyl compounds corresponding thereto, and so forth.

EXAMPLE 17

To a solution of 6 g. of methyl 5-acetyl-7-methyl-xanthene-2-carboxylate in 500 ml. of absolute methanol are added 1.1 g. of sodium borohydride in 50 ml. of water at a temperature of from 25° to 30°C with stirring, over a period of about 30 minutes. After 15 minutes under these conditions, 400 ml. of water and 20 ml. of acetic acid are added and the resultant mixture is stripped of solvent. The resultant mixture is extracted with methylene chloride and washed with bicarbonate and water. The washed extracts are concentrated to give methyl 5-(1-hydroxyethyl)-7-methylxanthene-2-carboxylate.

A solution of 5.5 g. of methyl 5-(1-hydroxyethyl)-xanthene-7-methylxanthene-2-carboxylate in 100 ml. of pyridine is cooled in an ice bath. To the cooled solution are added 2.91 ml. of acetyl chloride and the resultant mixture is stirred in an ice bath for ½ hour and then at room temperature for 1 hour. After this time, the reaction mixture is poured into dilute hydrochloric acid-ice and the precipitate is filtered off and washed to give methyl 5-(1-acetoxyethyl)-7-methylxanthene-2-carboxylate.

To a solution of 3 g. of methyl 5-(1-acetoxyethyl)-7-methylxanthene-2-carboxylate in 80 ml. of acetone are added 12 ml. of 8 N chromic acid in 8N sulfuric acid. The resultant mixture is stirred at room temperature for 1 ¼ hours. Excess chromic oxide is decomposed with aqueous sodium bisulfite and to the resultant mixture are added 500 ml. of water. The resultant mixture is stripped of solvent and extracted with methylene chloride. The methylene chloride extracts are washed with 10% aqueous sodium bicarbonate solution and the washed extracts are concentrated in vacuum to give methyl 5-(1-acetoxyethyl)-7-methylxanthone-2-carboxylate.

A solution of 2.70 g. of methyl 5-(1-acetoxyethyl)-7-methylxanthone-2-carboxylate in 300 ml. of a 10% potassium hydroxide 10% aqueous methanol solution is heated under reflux under a nitrogen atmosphere for a period of 1 hour. After this time, 40 ml. of concentrated hydrochloric acid in 70 ml. of water are added. Thereafter, 100 ml. of water are added and the resultant solution is stripped of solvent in vacuum and filtered to give 5-(1-hydroxyethyl)-7-methylxanthone-2-carboxylic acid.

In like manner, by subjecting the other 5-acyl xanthone-2-carboxylic compounds of Example 15 to the procedure of the present example, the corresponding products are prepared, e.g.:

5-(1-hydroxypropyl)-7-methylxanthone-2-carboxylic acid,
5-(1-hydroxyethyl)-7-ethylxanthone-2-carboxylic acid,
5-(1-hydroxypropyl)-7-ethylxanthone-2-carboxylic acid,
5-(1-hydroxyethyl)-7-n-propylxanthone-2-carboxylic acid,
5-(1-hydroxypropyl)-7-n-propylxanthone-2-carboxylic acid,
5-(1-hydroxyethyl)-7-isopropylxanthone-2-carboxylic acid,
5-(1-hydroxypropyl)-7-isopropylxanthone-2-carboxylic acid,
5-(1-hydroxyethyl)-7-n-octylxanthone-2-carboxylic acid,
5-(1-hydroxypropyl)-7-n-octylxanthone-2-carboxylic acid,
5-(1-hydroxyethyl)-7-methoxyxanthone-2-carboxylic acid,
5-(1-hydroxypropyl)-7-methoxyxanthone-2-carboxylic acid,
5-(1-hydroxyethyl)-7-ethoxyxanthone-2-carboxylic acid,
5-(1-hydroxypropyl)-7-ethoxyxanthone-2-carboxylic acid,
5-(1-hydroxyethyl)-7-n-propoxyxanthone-2-carboxylic acid,
5-(1-hydroxypropyl)-7-n-propoxyxanthone-2-carboxylic acid,
5-(1-hydroxyethyl)-7-isopropoxyxanthone-2-carboxylic acid,
5-(1-hydroxypropyl)-7-isopropoxyxanthone-2-carboxylic acid,
5-(1-hydroxyethyl)-7-n-octyloxyxanthone-2-carboxylic acid,
5-(1-hydroxypropyl)-7-n-octyloxyxanthone-2-carboxylic acid,
and the 5-(1-hydroxybutyl) compounds corresponding thereto, and so forth.

EXAMPLE 18

The procedure of Example 17 is repeated with the starting compounds of Example 16 to prepare the following:

5-methyl-7-(1-hydroxyethyl)-xanthone-2-carboxylic acid,
5-methyl-7-(1-hydroxypropyl)-xanthone-2-carboxylic acid,
5-ethyl-7-(1-hydroxyethyl)-xanthone-2-carboxylic acid,
5-ethyl-7-(1-hydroxypropyl)-xanthone-2-carboxylic acid,
5-n-propyl-7-(1-hydroxyethyl)-xanthone-2-carboxylic acid,
5-n-propyl-7-(1-hydroxypropyl)-xanthone-2-carboxylic acid,
5-isopropyl-7-(1-hydroxyethyl)-xanthone-2-carboxylic acid,
5-isopropyl-7-(1-hydroxypropyl)-xanthone-2-carboxylic acid,
5-n-octyl-7-(1-hydroxyethyl)-xanthone-2-carboxylic acid,
5-n-octyl-7-(1-hydroxypropyl)-xanthone-2-carboxylic acid,
5-methoxy-7-(1-hydroxyethyl)-xanthone-2-carboxylic acid,
5-methoxy-7-(1-hydroxypropyl)-xanthone-2-carboxylic acid,
5-ethoxy-7-(1-hydroxyethyl)-xanthone-2-carboxylic acid,
5-ethoxy-7-(1-hydroxypropyl)-xanthone-2-carboxylic acid,
5-n-propoxy-7-(1-hydroxyethyl)-xanthone-2-carboxylic acid,
5-n-propoxy-7-(1-hydroxypropyl)-xanthone-2-carboxylic acid,
5-isopropoxy-7-(1-hydroxyethyl)-xanthone-2-carboxylic acid,
5-isopropoxy-7-(1-hydroxypropyl)-xanthone-2-carboxylic acid,
5-n-octyloxy-7-(1hydroxyethyl)-xanthone-2-carboxylic acid,
5-n-octyloxy-7-(1-hydroxypropyl)-xanthone-2-carboxylic acid,
and the 7-(1-hydroxybutyl) compounds corresponding thereto, and so forth.

EXAMPLE 19

A mixture of 3 g. of 5,7-dimercaptoxanthone-2-carboxylic acid in 150 ml. of dimethylformamide, 5 ml. of methyl iodide and 5 ml. of potassium carbonate is stirred for 16 hours at 60°C. The mixture is then poured into dilute hydrochloric acid and the resultant mixture extracted with ethyl acetate. The extracts are chromatographed on alumina (methylene chloride) to give methyl 5,7-di(methylthio)-xanthone-2-carboxylate (i.e. methyl 5,7-di(thiomethoxy)-xanthone-2-carboxylate) which can be recrystallized from methylene chloride/methanol.

A mixture of 580 mg. of methyl 5,7-di(methylthio)-xanthone-2-carboxylate, 30 ml. of ethanol, 5 ml. of saturated sodium carbonate solution and 5 ml. of water is refluxed for 1 hour. The mixture is then cooled, acidified and the precipitate filtered off to give 5,7-di(-methylthio)-xanthone-2-carboxylic acid (i.e. 5,7-di(-thiomethoxy)-xanthone-2-carboxylic acid) as also prepared in the alternative method described in Example 1.

A mixture of 0.8 g. of 5,7-dimercapatoxanthone2-carboxylic acid, 2 ml. of 2-bromopropane, and excess potassium carbonate in 50 ml. of dimethylformamide is stirred for 24 hours at 75°C. Dilute hydrochloric acid and ethanol are added, the solid filtered off and washed. The solid is saponified with sodium carbonate in aqueous methanol (30 minutes reflux). The alkaline solution is diluted with water, treated with charcoal, filtered, and acidified to give 5,7-di(isopropylthio)-xanthone-2-carboxylic acid which can be recrystallized from tetrahydrofuran/ethyl acetate.

The foregoing are useful as an alternative to the method of Example 1 for the preparation of the compounds thereof which are useful as described in the above examples.

EXAMPLE 20

The compound 5,7-dimercaptoxanthone-2-carboxylic acid is treated by the procedure of Example 15, paragraph 1, to prepare 5,7-dimercaptoxanthone-2-carboxylic acid. This compound is treated in accordance with the procedure of Example 6 to give 5,7-di(-chlorosulfonyl)-xanthene-2-carboxylic acid. This compound is treated in accordance with the procedure of Example 15, paragraph 4, to give 5,7-di(chlorosulfonyl)-xanthone-2-carboxylic acid, which is useful as described in the above examples.

EXAMPLE 21

The compounds 5-alkyl(or 7-alkyl)-7-methoxy-(or 5-methoxy)-xanthone-2-carboxylic acid are prepared as described in Example 1. Thereafter, these compounds are treated in accordance with the procedure of Example 5, paragraph 2, to give 5-alkyl (or 7-alkyl)-7-hydroxy(or 5-hydroxy)-xanthone-2-carboxylic acid compounds which are useful as described in the above examples, c.f. Example 5.

EXAMPLE 22

The procedures of Example 1 are repeated to prepare the 5,7-dilower alkoxyxanthone-2-carboxylic acid compounds hereof. Alternatively, 5,7-dihydroxyxanthone-2-carboxylic acid is prepared as described in Example 5 and treated as follows:

5,7-Dihydroxyxanthone-2-carboxylic acid (1.3 g.) in 30 ml. of dimethylformamide containing 5g. of n-propylbromide and 5 g. of potassium carbonate is stirred at 60°C for 18 hours. The reaction mixture is then acidified and the acidified mixture partially evaporated in vacuum to remove excess n-propylbromide. The mixture is then filtered and the filtered precipitate washed and then dissolved in 100 ml. of ethanol. Twenty milliliters of 2N sodium hydroxide is then added and the resultant mixture refluxed for 60 minutes. The mixture is then cooled, diluted with water, and filtered. The filtrate is acidified and the acidified mixture evaporated to give 5,7-di(n-propoxy)-xanthone-2-carboxylic acid which is recrystallized from ethanol-water.

In a similar manner, the following are prepared:
5,7-diethoxyxanthone-2-carboxylic acid,
5,7-diisopropoxyxanthone-2-carboxylic acid,
5,7-di-n-butoxyxanthone-2-carboxylic acid,
5,7-di-sec-butoxyxanthone-2-carboxylic acid,
5,7-diisobutoxyxanthone-2-carboxylic acid,
5,7-di-t-butoxyxanthone-2-carboxylic acid,
5,7-dipentyloxyxanthone-2-carboxylic acid,
5,7-diisopentyloxyxanthone-2-carboxylic acid, and
5,7-dicyclopentyloxyxanthone-2-carboxylic acid.

EXAMPLE 23

The 5-lower alkyl(or 7-lower alkyl)-7-hydroxy(or 5-hydroxy)-xanthone-2-carboxylic acid products of Example 21 are subjected to the procedure of Example 22 to prepare the following compounds:
5-methyl-7-methoxyxanthone-2-carboxylic acid,
5-methyl-7-ethoxyxanthone-2-carboxylic acid,
5-methyl-7-n-propoxyxanthone-2-carboxylic acid,
5-methyl-7-isopropoxyxanthone-2-carboxylic acid,
5-methyl-7-n-butoxyxanthone-2-carboxylic acid,
5-methyl-7-isobutoxyxanthone-2-carboxylic acid,
5-methyl-7-sec-butoxyxanthone-2-carboxylic acid,
5-methyl-7-t-butoxyxanthone-2-carboxylic acid,
5-methyl-7-n-pentyloxyxanthone-2-carboxylic acid,
5-methyl-7-isopentyloxyxanthone-2-carboxylic acid,
5-methyl-7-cyclopentyloxyxanthone-2-carboxylic acid, and the corresponding eleven 7-alkoxy compounds in each of the 5-ethyl, -n-propyl, -isopropyl, -n-butyl, -isobutyl, -sec-butyl, -t-butyl, -n-pentyl, -isopentyl, -cyclopentyl and the corresponding 121 compounds in the 5-lower alkoxy-7-lower alkylxanthone-2-carboxylic acid series, e.g.:
5-methoxy-7-methylxanthone-2-carboxylic acid, and so forth.

EXAMPLE 24

A mixture of 51.5 g. of 1,3-dimethyl-4-iodobenzene (4-iodo-m-xylene), 40 g. of o,p-dimethoxyphenol, 16 g. of cuprous oxide in 300 ml. of dimethylacetamide is heated to the boiling point and maintained under reflux (190°C) for 144 hours with stirring and under a nitrogen atmosphere. The reaction mixture is then poured into ice water and extracted with ether and the extracts are filtered through 500 g. of alumina in hexane to give 1,33-dimethyl-4-(o,p-dimethoxyphenyloxy)-benzene.

A mixture of 41g. of 1,3-dimethyl-4-(o,p-dimethoxyphenyloxy)-benzene, 300 g. of potassium permanganate, 500 ml. of t-butanol, and 750 ml of water is heated to the boiling point and maintained thereat for a period of 3 hours. After distilling off the t-butanol, the reaction mixture is filtered, the clear filtrate acidified and the precipitate of 1,3dicarboxy-4(o,p-dimethoxyphenyloxy)-benzene is isolated by suction filtration and washed with water.

The 1,3-dicarboxy-4-(o,p-dimethoxyphenyloxy)-benzene thus prepared is then cyclized as described in Example 1 or 25 to give 5,7-dimethoxyxanthone-2-carboxylic acid which can be converted to 5,7-dihydroxyxanthone-2-carboxylic acid and/or thence to other compounds as described above.

In a similar manner, the foregoing procedure can be practiced utilizing other o-, p-, or o,p-lower alkoxyphenol starting compounds to prepare the corresponding products, for example,
5,7-di(ethoxy)-xanthone-2-carboxylic acid,
5,7-di(n-propoxy)-xanthone-2-carboxylic acid,
5,7-di(isopropoxy)-xanthone-2-carboxylic acid,
5,7-di(n-butoxy)-xanthone-2-carboxylic acid, and so forth, which can each be converted to other compounds hereof as described above.

EXAMPLE 25

A mixture of 1,3-dimethyl-4-bromobenzene, 10.5 g. of o,p-dimethoxyphenol, 4.65 g. of cuprous oxide, 40 ml. of tetramethylurea, and 75 ml. of N-methylpyrrolidene is stirred at 165° for 96 hours. The resultant mixture is diluted with water and extracted with methylene chloride. The methylene chloride extracts are chromatographed on 300 g. of alumina with gradient elution using hexane:ether to give 1,3-dimethyl-4-(o,p-dimethoxyphenyloxy)-benzene.

A mixture of 12 g. of 1,3-dimethyl-4-(o,p-dimethoxyphenyloxy)-benzene, 72 g. of potassium permanganate, 200 ml. of t-butanol and 350 ml. of water is refluxed for 4½ hours. After this time, the t-butanol is distilled off, and the reaction mixture is filtered. The filtrate is acidified to give 1,3-dicarboxy-4-(o,p-dimethoxyphenyloxy)-benzene which can be recrystallized from benzene:heptane.

A mixture of 3 g. of 1,3-dicarboxy-4-(o,p-dimethoxyphenyloxy)-benzene, 75 ml. of polyphosphoric acid, and 75 ml. of sulfolane is stirred at 125°C for a period of 2 hours. After this time, the reaction mixture is poured into water, filtered and the precipitate washed. The precipitate is recrystallized form acetic acid (charcoal) to give 5,7-dimethoxyxanthone-2-carboxylic acid which can be converted to 5,7-dihydroxyxanthone-2-carboxylic acid and/or thence to other compounds as described above.

EXAMPLE 26

A mixture of 2 g. of 5,7-di(1-hydroxyethyl)-xanthone-2-carboxylic acid in 20 ml. of pyridine and 10 ml. of acetyl chloride is heated at steam bath temperatures for 1 hour. The mixture is then poured into HCl/ice water and the solid which forms is collected by filtration, washed with water and dried to yield 5,7-di(1-acetoxyethyl)-xanthone-2-carboxylic acid.

Upon substitution of stoichiometrically appropriate amounts of the appropriate acyl chloride in the above procedure and, in addition, employing as starting compounds the products listed in Examples 10, 17 and 18, the following compounds are prepared:

5,7-di(1-propionyloxyethyl)-xanthone-2-carboxylic acid,
5,7-di(1-butyryloxyethyl)-xanthone-2-carboxylic acid,
5,7-di(1-acetoxy-n-propyl)-xanthone-2-carboxylic acid,
5,7-di(1-acetoxy-n-butyl)-xanthone-2-carboxylic acid,
5,7-di(1-acetoxy-isobutyl)-xanthone-2-carboxylic acid,
and so forth,
5-(1-acetoxyethyl)-7-methylxanthone-2-carboxylic acid,
5-(1-acetoxyethyl)-7-isopropylxanthone-2-carboxylic acid,
5-(1-acetoxyethyl)-7-n-octylxanthone-2-carboxylic acid,
5-(1-acetoxyethyl)-7-methoxyxanthone-2-carboxylic acid,
5-(1-acetoxyethyl)-7-isopropoxyxanthone-2-carboxylic acid,
5-(1-acetoxyethyl)-7-n-octyloxyxanthone-2-carboxylic acid,
and so forth,
5-methyl-7-(1-acetoxyethyl)-xanthone-2-carboxylic acid,
5-isopropyl-7-(1-acetoxyethyl)-xanthone-2-carboxylic acid,
5-n-octyl-7-(1-acetoxyethyl)-xanthone-2-carboxylic acid,
5-methoxy-7-(1-acetoxyethyl)-xanthone-2-carboxylic acid,
5-isopropoxy-71(1-acetoxyethhyl)-xanthone-2-carboxylic acid,
5-n-octyloxy-7-(1-acetoxyethyl)-xanthone-2-carboxylic acid,
and so forth,
5,7-di(cyclopropyl)acetoxymethyl)xanthone-2-carboxylic acid,
5,7-di(1-propionyloxyisobutyl)-xanthone-2-carboxylic acid,
5-methyl-7-((phenyl)acetoxymethyl)-xanthone-2-carboxylic acid, and
5-(1-acetoxyisobutyl)-7-isopropoxyxanthone-2-carboxylic acid.

EXAMPLE 27

Methyl 5,7-di(1-hydroxyethyl)-xanthone-2-carboxylate is prepared from the acid by the method of Example 2. To a mixture of 2.5 g. of methyl 5,7-di(1-hydroxyethyl)-xanthone-2-carboxylate and 1 g. of sodium hydride in 100 ml. of dimethyl-formamide is added 5 ml. of methyl iodide and the mixture is stirred at room temperature for 16 hours. The mixture is then poured into dilute HCl/ice water, filtered and dried to give methyl 5,7-di(1-methoxyethyl)-xanthone-2-carboxylate.

The resultant product is hydrolyzed according to the procedure of Paragraph B) of Example 1 to give 5,7-di(1-methoxyethyl)-xanthone-2-carboxylic acid.

Upon substitution of stoichiometrically appropriate amounts of the appropriate alkyl or cycloalkyl iodide or bromide and, in addition, employing as starting compounds the products listed in Examples 10, 17 and 18, the following compounds are prepared, through their respective esters:

5,7-di(1-ethoxyethyl)-xanthone-2-carboxylic acid, 7
5,7-di(1-methoxy-n-propyl)-xanthone-2-carboxylic acid,
5,7-di(1-ethoxy-n-propyl)-xanthone-2-carboxylic acid,
5,7-di(1-methoxyisobutyl)-xanthone-2-carboxylic acid,
5,7-di(1-isopropoxyethyl)-xanthone-2-carboxylic acid,
5,7-di(1-isopropoxy-n-propyl)-xanthone-2-carboxylic acid,
5,7-di(1-isopropoxyisobutyl)-xanthone-2-carboxylic acid,
5,7-di(1-cyclopentyloxyethyl)-xanthone-2-carboxylic acid,
5,7-di(1 cyclopentyloxy-n-propyl)-xanthone-2-carboxylic acid,
5-methyl-7-(1-methoxyethyl)-xanthone-2-carboxylic acid,
5-methoxy-7-(1-methoxyethyl)-xanthone-2-carboxylic acid,
5-isopropyl-7-(1-methoxyethyl)-xanthone-2-carboxylic acid,
5-n-octyl-7-(1-methoxyethyl)-xanthone-2-carboxylic acid, 5-isopropoxy-7-(1-methoxyethyl)-xanthone-2-carboxylic acid,
5-n-octyloxy-7-(1-methoxyethyl)-xanthone-2-carboxylic acid,
5-isopropyl-7-(1-ethoxyethyl)-xanthone-2-carboxylic acid,
5-isopropoxy-7-(1-ethoxyethyl)-xanthone-2-carboxylic acid,
5-(1-methoxyethyl)-7-methylxanthone-2-carboxylic acid,
5-(1-methoxyethyl)-7-methoxyxanthone-2-carboxylic acid,
5-(1-methoxyethyl)-7-isopropylxanthone-2-carboxylic acid,
5-(1-methoxyethyl)-7-isopropoxyxanthone-2-carboxylic acid,
5-(1-ethoxyethyl)-7-isopropylxanthone-2-carboxylic acid,
5-(1-ethoxyethyl)-7-isopropoxyxanthone-2-carboxylic acid,
5-methoxy-7-(1-methoxy-n-butyl)-xanthone-2carboxylic acid,
5-(1-methoxy-n-butyl)-7-methoxyxanthone-2-carboxylic acid,
5-isobutyl-7-(1-ethoxyisobutyl)-xanthone-2-carboxylic acid,
5-(1-methoxyisobutyl)-7-isopropylxanthone-2-carboxylic acid,
5,7-di((cyclopropyl)methoxymethyl)-xanthone-methoxymethyl)-xanthone-2-carboxylic acid,
5-((cyclopropyl)methoxymethyl)-7-cyclopropylxanthone2-carboxylic acid,
5, 7-di((phenyl)methoxymethyl)-xanthone-2-carboxylic acid,
5-isopropoxy-7-((phenyl)methoxymethyl)-xanthone-2-carboxylic acid,
5-n-octyloxy-7-((phenyl)methoxymethyl)-xanthone-2-carboxylic acid,
5, 7-di(1-propoxyethyl)-xanthone-2-carboxylic acid, and
5-(1-isopropoxyethyl)-7-methylxanthone-2-carboxylic acid.

EXAMPLE 28

A mixture of 1.6 g. of methyl 5, 7-di(1-hydroxyethyl)-xanthone-2-carboxylate, 100 ml. of methylene chloride, 100 ml. of isobutene and 2 ml. of $BF_3/H_3PO_4$ catalyst are shaken in a pressure bottle for 4 days at room temperature. The reaction mixture is diluted with methylene chloride, washed with bicarbonate solution, then water, dried and evaporated and crystallized from methanol to give methyl 5, 7-di(1-t-butoxyethyl)-xanthone-2-carboxylate.

Hydrolysis provides 5, 7-di(1-t-butoxyethyl)-xanthone-2-carboxylic acid.

Likewise, the following products are prepared from the respective starting compounds:
5, 7-di(1-t-butoxy-n-propyl)-xanthone-2-carboxylic acid,
5, 7-di(1-t-butoxyisobutyl)-xanthone-2-carboxylic acid,
5, 7-di(1-t-butoxy-n-propyl)-xanthone-2-carboxylic acid,
5-(1-t-butoxyethyl)-7-methoxyxanthone-2-carboxylic acid,
5-(1-t-butoxyethyl)-7-isopropoxyxanthone-2-carboxylic acid,
5, 7-di((cyclopropyl)-t-butoxymethyl)-xanthone-2-carboxylic acid,
5-((cyclopropyl)-t-butoxymethyl)-7-isopropylxanthone-2-carboxylic acid,
5, 7-di((phenyl)-t-butoxymethyl)-xanthone-2-carboxylic acid,
5-methyl-7-((phenyl)-t-butoxymethyl)-xanthone-2-carboxylic acid,
5-isopropyl-7-(1-t-butoxyethyl)-xanthone-2-carboxylic acid,
5-isopropoxy-7-(1-t-butoxyethyl-xanthone 2-carboxylic acid, and
5-n-octyloxy-71(11t-butoxyethyl)-xanthone-2-carboxylic acid.

EXAMPLE 29

Twenty milliliters of dihydropyran are added to a solution of 1 g. of methyl 5, 7-di(1-hydroxyethyl)-xanthone-2-carboxylate in 100 ml. of benzene. About 1 ml. is removed by distillation to remove moisture and 0.8 g. of p-toluenesulfonic acid is added to the cooled solution. This mixture is allowed to stand at room temperature for 4 days, and is then washed with aqueous sodium carbonate solution and water, dried and evaporated. The residue is crystallized from chloroform/methanol/pyridine to yield methyl 5, 7-di(1-tetrahydrophyran-2'-yloxyethyl)-xanthone-2-carboxylate.

Hydrolysis provides 5, 7-di(1-tetrahydropyran-2'-yloxyethyl)-xanthone-2carboxylic acid.

By use of dihydrofuran in the above procedure, 5, 7-di-(1-tetrahydrofuran-2'-yloxyethyl)-xanthone-2-carboxylic acid is prepared.

In like manner, the following compounds are prepared:
5-methyl-7-(1-tetrahydropyrane-2'-yloxyethyl)-xanthone-2-carboxylic acid,
5-methoxy-7-(1-tetrahydropyran-2'-yloxyethyl)-xanthone12-carboxylic acid,
5-isopropyl-7-(1-tetrahydropyran-2'-yloxyethyl)-xanthone-2-carboxylic acid,
5-isopropoxy-7-(1-tetrahydropyran-2'-yloxyethyl)-xanthone-2-carboxylic acid,
5-n-octyloxy-7-(1-tetrahydropyran-2'-yloxyethyl)-xanthone-2-carboxylic acid, and the tetrahydrofuran-2'-yloxy compounds corresponding thereto,
5-(1-tetrahhydropyran-2'-yloxyethyl)-7-methylxanthone-2-carboxylic acid,
5-(1-tetrahydropyran-2'-yloxyethyl)-7-methoxyxanthone- 2-carboxylic acid,
5-(1-tetrahydropyran-2'-yloxyethyl)-7-isopropylxanthone-2-carboxylic acid,
5-(1-tetrahydropyran-2'-yloxyethyl)-7-isopropoxyxanthone-2-carboxylic acid,
5-(1-tetrahydropyran-2'-yloxyethyl)-7-n-octyloxyxanthone-2-carboxylic acid, and the tetrahydrofuran-2'-yloxy compounds corresponding thereto,
5, 7-di(1-tetrahydropyran-2'-yloxy-n-propyl)-xanthone-2-carboxylic acid,
5, 7-di(1-tetrahydropyran-2'-yloxy-isobutyl)-xanthone-2-carboxylic acid, and
5, 7-di(1-tetrahydrofuran-2'-yloxy-n-propyl)-xanthone-2-carboxylic acid.

3.5 Grams of methyl 5, 7-di(1-hydroxyethyl)-xanthone-2-carboxylate in 150 ml. of benzene and 1 g. of p-toluenesulfonic acid (dried by azeotropic distillation from benzene are mixed together and the reaction mixture is treated with 4-methoxy-5, 6-dihydro-2H-pyron, 1ml. at a time until reaction is complete (followed by tlc). The reaction is quenched by addition of ½ ml. of triethylamine, washed with water, and crystallized with care from methanol containing pyridine to give methyl 5, 7-di(1-4'-methoxytetrahydropyran-4'-yloxyethyl)-xanthone-2-carboxylate.

Hydrolysis provides 5, 7-di(1-4'-methoxytetrahydropyran-4'-yloxyethyl)-xanthone-2-carboxylic acid.

A solution of 3.0 g. of aluminum chloride in 50 ml. of tetrahydrofuran is treated with a solution of 0.8 g. of lithium aluminum hydride in 100 ml. of tetrahydrofuran. Methyl 5, 7-di(1-4'-methoxytetrahydropyran-4'-yloxyethyl)-xanthone-2-carboxylate (500 mg.) is extracted into the solution. After reduction is complete (monitored by tlc), saturated sodium chloride is added until a precipitate forms. This is filtered and the crude product is oxidized in acetic acid using excess sodium dichromate to give 5, 7-1-tetrahydropyran-4'-yloxyethyl)-xanthhone-2-carboxylic acid.

In like manner, the following compounds are prepared:

5, 7-di(1-4'-methoxytetrahydropyran-4'-yloxy-n-propyl)-xanthone-2-carboxylic acid, 5, 7-di(1-tetrahydropyran-4'-yloxy-n-propyl)-xanthone-2-carboxylic acid, 5, 7-di(1-4'-ethoxytetrahydropyran-4'-yloxyethyl)-xanthone-2-carboxylic acid, 5, 7-di(1-4'-methoxytetrahydropyran-4'-yloxyisobutyl-xanthone -2-carboxylic acid, 5-isopropyl-7-(1-4'-methoxytetrahydropyran-4'yloxyethyl)-xanthone-2-carboxylic acid, 5-isopropoxy-7-(1-tetrahydropyran-4'-yloxyethyl)-xanthone-2-carboxylic acid, 5-(1-tetrahydropyran-4'-yloxyethyl)-7-isopropyl-xanthone-2-carboxylic acid, 5-1-tetrahydropyran-4'-yloxyethyl)-7-isopropoxyxanthone-2-carboxylic 5-(1-4'-propoxytetrahydropyran-4'-yloxy-n-propyl)-7-methylxanthone-2-carboxylic acid, and 5-methoxy-7-1-tetrahydropyran-4'-yloxyethyl)-xanthone- 2-carboxylic acid, and 5-n-octyloxy-7-(1-tetrahydropyran-4'-yloxyethyl)-xanthone-2-carboxylic acid.

EXAMPLE 30

A mixture of 4.5 g. of 5, 7-di(methylsulfinyl)-xanthone-2-carboxylic acid, 10 g. of methyl iodide, and 10 g. of lithium carbonate in 75 ml. of dimethylformamide is stirred at room temperature for a period of 18 hours. After this period of time, the reaction mixture is poured into dilute hydrochloric acid-ice and the resultant precipitate is filtered off and washed to give methyl 5, 7-di(methylsulfinyl)-xanthone12-carboxylate.

The foregoing procedure is repeated using the alternate lower alkyl iodides so as to prepare the corresponding lower alkyl acid esters hereof, e.g.:

ethyl 5, 7-di(methylsulfinyl)-xanthone-2-carboxylate, n-propyl 5, 7-di(methylsulfinyl)-xanthone-2-carboxylate, isopropyl 5, 7-di(methylsulfinyl)-xanthone-2-carboxylate, n-propyl 5, 7-di(methylsulfinyl)-xanthone-2-carboxylate, isobutyl 5, 7-di(methylsulfinyl)-xanthone-2-carboxylate, sec-butyl 5, 7-di(methylsulfinyl)-xanthone-2-carboxylate, n-pentyl 5, 7-di(methylsulfinyl)-xanthone-2-carboxylate, and so forth.

In like manner, the other xanthone-2-carboxylic acids hereof containing substituents at the C5, 7 positions, prepared as described above, can be converted to the corresponding acid esters, e.g:

methyl 5, 7-di(methylsulfonyl)-xanthone-2-carboxylate, ethyl 5-methylsulfonyl-7-isopropoxyxanthone-2-carboxylate n-propyl 5, 7-disulfamoylxanthone-2-carboxylate, methyl 5-acetyl-7-ethylxanthone-2-carboxylate, and so forth.

In the sulfo series, the esters are prepared by treating the acid with the appropriate lower alkanol under reflux and in the absence of acid to give, e.g:

methyl 5, 7-disulfoxanthone-2-carboxylate, and ethyl 5, 7-disulfoxanthone-2-carboxylate.

EXAMPLE 31

To a solution of 10 g. of 5, 7-di(methylsulfinyl)-xanthone-2-carboxylic acid in 200 ml. of ethanol is added the theoretical amount of sodium hydroxide dissolved in 200 ml. of 90% ethanol. The reaction mixture is then concentrated in vacuum to give sodium 5, 7-di(methylsulfinyl)-xanthone-2-carboxylate.

In a similar manner, the potassium and lithium salts are prepared. Similarly, by replacing the sodium salt by means of an appropriate metal salt reagent, e.g. calcium chloride, manganese chloride, and so forth, the other xanthone-2-carboxylic acid salts are prepared, e.g.:

magnesium 5, 7-di(methylsulfinyl)-xanthone-2-carboxylate, calcium 5, 7-di(methylsulfinyl)-xanthone-2-carboxylate, aluminum 5, 7-di(methylsulfinyl)-xanthone-2-carboxylate, ferrous 5, 7-di(methylsulfinyl)-xanthone-2-carboxylate, zinc 5, 7-di(methylsulfinyl)-xanthone-2-carboxylate, manganese 5, 7-di(methylsulfinyl)-xanthone-2-carboxylate, ferric 5, 7-di(methylsulfinyl)-xanthone-2-carboxylate, and so forth.

In a similar manner, the xanthone-2-carboxylic acid salts of the other C-5, 7disubstituted xanthone-2-carboxylic acids hereof are prepared, e.g.:

potassium 5, 7-di(methylsulfonyl)-xanthone-2-carboxylate, sodium 5-isopropyl-7-methylsulfinylxanthone-2-carboxylate, potassium 5, 7-di(1-hydroxyethyl)-xanthone-2-carboxylate, sodium 5, 7-sulfamoylxanthone-2-carboxylate, sodium 5-isopropoxy-7-methylsulfinylxanthone-2-carboxylate, sodium 5-isopropoxy-7-acetylxanthone-2-carboxylate, sodium 5-methylsulfonyl-7-isopropoxyxanthone-2-carboxylate, sodium 5-methylsulfinyl-7-isopropoxyxanthone-2-carboxylate, sodium 5-butoxy-7-methylsulfonylxanthone-2-carboxylate, sodium 5-acetyl -7-isopropoxyxanthone-2-carboxylate, sodium 5-cyclopentyloxy-7-methylsulfinylxanthone-2-carboxylate, sodium 5-n-pentyloxy-7-methylsulfinylxanthone-2-carboxylate, sodium 5-isopentyloxy-7-methylsulfinylxanthone-2-carboxylate, sodium 5-n-octyloxy-7-methylsulfinylxanthone-2-carboxylate, and so forth.

In the sulfo series, use of one equivalent of base provides the sulfo acid salt and use of two or more equivalents provides the disalt, e.g. 5, 7-disulfoxanthone-2-carboxylic acid disodium salt.

EXAMPLE 32

To a mixture of 50 ml. of concentrated aqueous ammonia in 500 ml. of methanol there are added 20 g. of 5, 7-disulfamoylxanthone-2-carboxylic acid. The resultant mixture is stirred for 2 hours and is then evaporated to dryness to give the ammonium salt of 5, 7-disulfamoylxanthone-2-carboxylic acid.

A solution of 10 g. of 5, 7-disulfamoylxanthone-2-carboxylic acid in 50 ml. of thionyl chloride is heated at reflux for 1 hour. Thereafter, the solution is evaporated to dryness to give the corresponding acid chloride to which is added a concentrated ethereal ammonia solution. The resultant solution is evaporated giving the the 5, 7 -disulfamoylxanthone-2-carboxylic acid amide.

In like manner, the lower alkyl amides can be prepared using monoalkylamine or dialkylamine in lieu of ammonia in the above procedures. Thus prepared, are, e.g.:

5, 7-di(methylsulfamoyl)-xanthone-2-carboxylic acid amide,

N-methyl 5, 7-di(n-propylsulfinyl-xanthone-2-carboxylic acid amide,

N,N-dimethyl 5-(dimethylsulfamoyl)-7-methylxanthone-2-carboxylic acid amide,

N,N-diethyl 5, 7-di(ethylsulfonyl)-xanthone-2-carboxylic acid amide,

N,N-diethyl 5, 7-diacetylxanthone -2-carboxylic acid amide,

N-ethyl 5-ethoxy-7-sulfoxanthone-2-carboxylic acid amide,

N-n-propyl 5-propyl-7-(propylsulfinyl)-xanthone-2-carboxylic acid amide, and so forth.

EXAMPLE 33

To a mixture of 20 g. of procaine and 500 ml. of aqueous methanol are added 20 g. of 5, 7-di(methylsulfinyl)-xanthone-2-carboxylic acid. The resultant mixture is stirred at room temperature for 16 hours. It is then evaporated under reduced pressure, to give the procaine salt of 5, 7-di(methylsulfinyl)- xanthone-2-carboxylic acid.

Similarly, the lysine, caffeine, and arginine salts thereof are obtained. In like manner, the e.g. procaine, lysine, caffeine, and arginine, salts of the other C-5, 7 disubstituted xanthone-2-carboxylic acids are obtained, e.g.:

the procaine salt of 5, 7-di(ethylsulfonyl)-xanthone-2-carboxylic acid, the caffeine salt of 5-(propylsulfinyl)-7-n-butoxyxanthone-2-carboxylic acid, the lysine salt of 5,7-di(di-t-butylsulfamoyl)-xanthone-2-carboxylic acid, the procaine salt of 5-(sec-butylsulfinyl)-7-sec-butoxyxanthone-2-carboxylic acid, and the arginine salt of 5,7-disulfoxanthone-2-carboxylic acid.

EXAMPLE 34

The following procedures illustrate the method by which the pharmaceutical compositions of the compounds hereof are prepared.

Sodium chloride (0.44 g.) is dissolved in 80 ml. of a (9.47 g/l. water) sodium hydrogen phosphate solution. A sodium dihydrogen phosphate (8.00 g/l. water) solution (20 ml.) is then added thereto. The resultant solution having a pH of 7.38 is sterilized in an autoclave. This vehicle is then added to solid, dry 5,7-di(methylsulfinyl)-xanthone-2-carboxylic acid to give a preparation suitable for intravenous injection containing 2.5 mg. of 5,7-di(methylsulfinyl)-xanthone-2-carboxylic acid per ml. of total composition.

EXAMPLE 35

The following procedure illustrates a test procedure for the compounds hereof.

Nornal female (Sprague-Dawley) rats of 150 to 200 grams each are passively sensitized intradermally by injection of rat anti-egg albumin reaginic sera. After 24 hours, each rat is challenged intravenously with 1 ml. of 0.5% Evans blue, 1 mg. egg albumin plus 10 mg. of 5,7-di(methylsulfinyl)-xanthone-2-carboxylic acid. Control rats receive no 5,7-di(methylsulfinyl)-xanthone-2-carboxylic acid. The dermal bluing is recorded 15 to 25 minutes later. The rats which receive the 5,7-di(methylsulfinyl)-xanthone-2-carboxylic acid exhibit a 100% inhibition of allergic reaction whereas the control rats exhibit no inhibition.

The above procedure is repeated using 5,7-di(methylsulfonyl)-xanthone-2-carboxylic acid, with similar results. The above procedure is repeated using oral administration, with similar results.

The C-5,7 disubstituted xanthone-2-carboxylic acid compounds are administered by gavage at a dose of 20 mg. per animal 15 minutes prior to challenge. 20 to 30 minutes after challenge the degree of dermal bluing is read, with similar results.

Inhibition of reaginic antigen-antibody reactions in rats is regarded as representative of inhibition of human reaginic antigen-antibody reactions which occur during allergic episodes.

Subjects challenged by antigen inhalation are measured for the extent of provoked degree of asthma condition by changes in airway resistance on expiration. The subject compounds are administered as an aerosol by inhalation before antigen challenge. Prevention of asthmatic conditions upon the administration of the compounds is evidenced by a decrease in airway resistance and other, subjective improvements, e.g. reduced cough.

EXAMPLE 36

A. To a suspension of 14.5 g. 5-methoxy-7-(methylthio)-xanthone-2-carboxylic acid in 350 ml. of acetic anhydride, 100 ml. 47% hydriodic acid is added dropwise with ice cooling. After refluxing the resulting mixture for 20 hours, it is diluted with 750 ml. of hot water and cooled. The yellow product is filtered off, washed with water and dried to give 12.8 g. 5-hydroxy-7-(methylthio)-xanthone-2-carboxylic acid.

Similarly, substituting 5-methylthio-7-methoxyxanthone-2-carboxylic acid for 5-methoxy-7-(methylthio)-xanthone-2-carboxylic acid yields 5-methylthio-7-hydroxyxanthone-2-carboxylic acid.

In like manner, other 5-hydroxy-7-(lower alkylthio)-xanthone-2-carboxylic acids and 5-lower alkylthio-7-hydroxyxanthone-2-carboxylic acids are obtained.

B. A mixture of 6.65 g. of 5-hydroxy-7-(methylthio)-xanthone-2-carboxylic acid, 4.5 g. of dry lithium carbonate, 4 ml. of methyl iodide and 70 ml. of dimethylformamide is stirred at room temperature for 20 hours. After adding an excess of acetic acid/water (1:1), excess methyl iodide is removed on a rotary evaporator. The crystalline product is filtered off, washed and dried to give 6.8 g. of methyl 5-hydroxy-7-(methylthio)-xanthone-2-carboxylate.

Similarly, substituting 5-methylthio-7-hydroxyxanthone-2-carboxylic acid in the foregoing procedure yields methyl 5-methylthio-7-hydroxyxanthone-2-carboxylate.

The foregoing procedure is repeated using the alternate lower alkyl iodides so as to prepare the lower alkyl acid esters hereof, e.g., ethyl 5-hydroxy-7-(methylthio)-xanthone-2-carboxylate, pentyl 5-hydroxy-7-(methylthio)-xanthone-2-carboxylate, and ethyl 5-methylthio-7-hydroxyxanthone-2-carboxylate, and pentyl-5-methylthio-7-hydroxyxanthone-2-carboxylate.

C. 1.55 g. of methyl 5-hydroxy-7-(methylthio)-xanthone-2-carboxylate is stirred at room temperature with 2.5 g. of octyl bromide and 1.0 g. of potassium carbonate in 30 ml. of dimethylformamide for 18 hours. After acidification with dilute hydrochloric acid, the mixture is extracted with chloroform, the extracts washed with water, dried over magnesium sulfate, and evaporated. Filtration of a chloroform solution of the crude product through alumina (activity II) afforded 2.0 g. of methyl 5-n-octyloxy-7-(methylthio)-xanthone-2-carboxylate.

Similarly, substituting methyl 5-methylthio-7-hydroxyxanthone-2-carboxylate in the foregoing procedure yields methyl 5-methylthio-7-n-octyloxyxanthone-2-carboxylate.

The foregoing procedure is repeated using other higher alkyl bromides so as to prepare the 5- and 7-higher alkoxy compounds e.g., methyl 5-n-hexyloxy-7-(methylthio)-xanthone-2-carboxylate,
methyl 5-n-heptyloxy-7-(methylthio)-xanthone-2-carboxylate,
methyl 5-n-dodecyloxy-7-(methylthio)-xanthone-2-carboxylate, and
methyl 5-methylthio-7-n-hexyloxyxanthone-2-carboxylate,
methyl 5-methylthio-7-n-heptyloxyxanthone-2-carboxylate, and
methyl 5-methylthio-7-n-dodecyloxyxanthone-2-carboxylate.

In like manner, other lower alkyl esters may be substituted for the methyl ester, and with the use of the appropriate higher alkyl bromide, there is obtained, for example, ethyl 5-n-octyloxy-7-(methylthio)-xanthone-2-carboxylate, pentyl 5-n-octyloxy-7-(methylthio)-xanthone-2-carboxylate, ethyl 5-n-hexyloxy-7-(methylthio)-xanthone-2-carboxylate, pentyl 5-n-heptyloxy-7-(methylthio)-xanthone-2-carboxylate, ethyl 5-n-dodecyloxy-7-(methylthio)-xanthone-2-carboxylate,
ethyl 5-methylthio-7-n-octyloxyxanthone-2carboxylate,
pentyl 5-methylthio-7-n-octyloxyxanthone-2-carboxylate,
ethyl 5-methylthio-7-n-hexyloxyxanthone-2-carboxylate,
pentyl 5-methylthio-7-n-hexyloxyxanthone-2-carboxylate, and
ethyl 5-methylthio-7-n-dodecyloxyxanthone-2-carboxylate.

D. To 2.0 g. of methyl 5-n-octyloxy-7-(methylthio)-xanthone-2-carboxylate in 60 ml. of chloroform there is slowly added a solution of 910 mg. of m-chloroperoxybenzoic acid in 40 ml. of chloroform while keeping the temperature at about 0°C. After the addition is complete, the solution is filtered through alumina (activity III) and evaporated to give 2.0 g. of methyl 5-n-octyloxy-7-methylsulfinylxanthone-2-carboxylate.

Similarly, substituting methyl 5-methylthio-7-n-octyloxyxanthone-2-carboxylate in the foregoing procedure yields methyl 5-methylsulfinyl-7-n-octyloxyxanthone-2-carboxylate.

Likewise, substituting the other compounds prepared in Part C of this example for 5-n-octyloxy-7-(methylthio)-xanthone-2-carboxylate, is productive of, for example, methyl 5-n-hexyloxy-7-methylsulfinylxanthone-2-carboxylate,
methyl 5-n-heptyloxy-7-methylsulfinylxanthone-2-carboxylate,
methyl 5-n-dodecyloxy-7-methylsulfinylxanthone-2-carboxylate,
ethyl 5-n-octyloxy-7-methylsulfinylxanthone-2carboxylate,
pentyl 5-n-octyloxy-7-methylsulfinylxanthone-2-carboxylate,
ethyl 5-n-hexyloxy-7-methylsulfinylxanthone-2-carboxylate,
pentyl 5-n-heptyloxy-7-methylsulfinylxanthone-2-carboxylate, and
ethyl 5-n-dodecyloxy-7-methylsulfinylxanthone-2-carboxylate, and
methyl 5-methylsulfinyl-7-n-heptyloxyxanthone-2-carboxylate,
methyl 5-methylsulfinyl-7-n-heptyloxyxanthone-2-carboxylate,
methyl 5-methylsulfinyl-7-n-dodecyloxyxanthone-2-carboxylate,
ethyl 5-methylsulfinyl-7-n-octyloxyxanthone-2-carboxylate,
pentyl 5-methylsulfinyl-7-n-octyloxyxanthone-2-carboxylate,
ethyl 5-methylsulfinyl-7-n-hexyloxyxanthone-2-carboxylate,
pentyl 5-methylsulfinyl-7-n-hexyloxyxanthone-2-carboxylate, and
ethyl 5-methylsulfinyl-7-n-dodecyloxyxanthone-2-carboxylate.

E. Methyl 5-n-octyloxy-7-(methylthio)-xanthone-2-carboxylate (750 mg.), 2 ml. of hydrogen peroxide (30%), and 40 ml. of acetic acid are heated on a steam bath (80°C) for 90 minutes. Tlc indicates the absence of starting material. The mixture is diluted with 60 ml. of hot water, and the mixture is cooled, the solid is filtered off and dried to give methyl 5-n-octyloxy-7-methylsulfonylxanthone-2-carboxylate which can be recrystallized from acetic acid/water.

Similarly, substituting methyl 5-methylthio-7-n-octyloxy-2-carboxylate in the foregoing procedure yields methyl 5-methylsulfonyl-7-n-octyloxyxanthone-2-carboxylate.

Likewise, substituting the other compounds prepared in Part C of this example for 5-n-octyloxy-7-(methylthio)-xanthone-2-carboxylate, is productive of, for example,
   methyl 5-n-hexyloxy-7-methylsulfonylxanthone-2-carboxylate,
   methyl 5-n-heptyloxy-7-methylsulfonylxanthone-2-carboxylate,
   methyl 5-n-dodecyloxy-7-methylsulfonylxanthone-2-carboxylate,
   ethyl 5-n-octyloxy-7-methylsulfonylxanthone-2-carboxylate,
   pentyl 5-n-octyloxy-7-methylsulfonylxanthone-2-carboxylate,
   ethyl 5-n-hexyloxy-7-methylsulfonylxanthone-2-carboxylate,
   pentyl 5-n-heptyloxy-7-methylsulfonylxanthone-2-carboxylate, and
   ethyl 5-n-dodecyloxy-7-methylsulfonylxanthone-2-carboxylate, and
   methyl 5-methylsulfonyl-7-n-hexyloxyxanthone-2-carboxylate,
   methyl 5-methylsulfonyl-7-n-heptyloxyxanthone-2-carboxylate,
   methyl 5-methylsulfonyl-7-n-dodecyloxyxanthone-2-carboxylate,
   ethyl 5-methylsulfonyl-7-n-octyloxyxanthone-2-carboxylate,
   pentyl 5-methylsulfonyl-7-n-octyloxyxanthone-2-carboxylate,
   ethyl 5-methylsulfonyl-7-n-hexyloxyxanthone-2-carboxylate,
   pentyl 5-methylsulfonyl-7-n-hexyloxyxanthone-2-carboxylate, and
   ethyl 5-methylsulfonyl-7-n-dodecyloxyxanthone-2-carboxylate.

F. 2.0 G. of methyl 5-n-octyloxy-7-methylsulfinylxanthone-2-carboxylate is refluxed for 30 minutes with 0.5 g. of potassium hydroxide in 80 ml. ethanol containing 20 ml. water. After acidifying with dilute hydrochloric acid, the precipitate is isolated by suction filtration and recrystallized from tetrahydrofuran/ethanol to give 1.8 g. 5-n-octyloxy-7-methylsulfinylxanthone-2-carboxylic acid.

Likewise, substituting as starting material the other compounds obtained in Parts D and E of this example for methyl 5-n-octyloxy-7-methylsulfinylxanthone-2-carboxylate, there is obtained, for example,
   5-methylsulfinyl-7-n-octyloxyxanthone-2-carboxylic acid,
   5-n-octyloxy-7-methylsulfonylxanthone-2-carboxylic acid,
   5-methylsulfonyl-7-n-octyloxyxanthone-2-carboxylic acid,
   5-n-hexyloxy-7-methylsulfinylxanthone-2-carboxylic acid,
   5-n-heptyloxy-7-methylsulfinylxanthone-2-carboxylic acid,
   5-n-dodecyloxy-7-methylsulfinylxanthone-2-carboxylic acid,
   5-methylsulfinyl-7-n-hexyloxyxanthone-2-carboxylic acid,
   5-methylsulfinyl-7-n-heptyloxyxanthone-2-carboxylic acid, and
   5-methylsulfinyl-7-n-dodecyloxyxanthone-2-carboxylic acid,
   5-n-hexyloxy-7-methylsulfonylxanthone-2-carboxylic acid,
   5-n-heptyloxy-7-methylsulfonylxanthone-2-carboxylic acid,
   5-n-dodecyloxy-7-methylsulfonylxanthone-2-carboxylic acid,
   5-methylsulfonyl-7-n-hexyloxyxanthone-2-carboxylic acid,
   5-methylsulfonyl-7-n-heptyloxyxanthone-2-carboxylic acid, and
   5-methylsulfonyl-7-n-dodecyloxyxanthone-2-carboxylic acid.

What is claimed is:

1. A compound selected from those represented by the following formula:

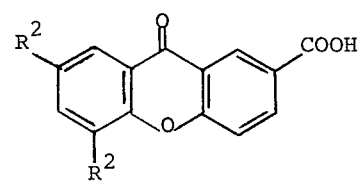

and the pharmaceutically acceptable, non-toxic alkyl or glycerol esters, amides, and salts thereof;
   wherein one $R^2$ group is alkoxy and the other $R^2$ group is lower alkanoyl.

2. The compound according to claim 1 of the formula:

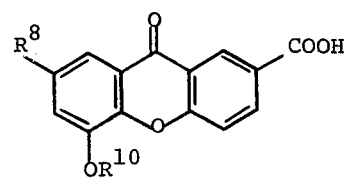

wherein $R^8$ is lower alkanoyl; and $R^{10}$ is alkyl.

3. The compound according to claim 2 wherein $R^8$ is acetyl and $R^{10}$ is isopropyl; 5-isopropoxy-7-acetylxanthone-2-carboxylic acid.

4. The compound according to claim 2 wherein $R^8$ is cyclopropylcarbonyl and $R^{10}$ is isopropyl; 5-isopropoxy-7-cyclopropylcarbonylxanthone-2-carboxylic acid.

5. The compound according to claim 1 of the formula:

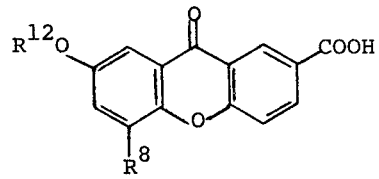

wherein $R^8$ is lower alkanoyl; and $R^{12}$ is alkyl.

6. The sodium salts of the compounds according to claim 1.

7. The compound according to claim 5 wherein $R^8$ is acetyl and $R^{12}$ is isopropyl; 5-acetyl-7-isopropoxyxanthone- 2-carboxylic acid.

* * * * *